(12) United States Patent
Okada et al.

(10) Patent No.: US 7,439,266 B2
(45) Date of Patent: Oct. 21, 2008

(54) MALONONITRILE COMPOUND AND USE THEREOF

(75) Inventors: Satoshi Okada, Takarazuka (JP); Daisuke Oohira, Toyonaka (JP); Ken Otaka, Iwaki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 504 days.

(21) Appl. No.: 10/522,764

(22) PCT Filed: Aug. 26, 2003

(86) PCT No.: PCT/JP03/10726

§ 371 (c)(1),
(2), (4) Date: Feb. 1, 2005

(87) PCT Pub. No.: WO2004/020399

PCT Pub. Date: Mar. 11, 2004

(65) Prior Publication Data

US 2006/0004092 A1    Jan. 5, 2006

(30) Foreign Application Priority Data

Aug. 29, 2002 (JP) .............................. 2002-250355

(51) Int. Cl.
*A01N 37/34* (2006.01)
*C07C 333/00* (2006.01)
*C07C 327/00* (2006.01)
*C07C 255/00* (2006.01)

(52) U.S. Cl. ........................ 514/521; 558/230; 558/235; 558/441

(58) Field of Classification Search .................. 514/521; 558/441, 230, 235
See application file for complete search history.

(56) References Cited

FOREIGN PATENT DOCUMENTS

JP          10-29966          2/1998

OTHER PUBLICATIONS

Roepel, Michael, "A one-pot radical addition/fragmentation route to ketones and esters" *Tetrahedron Letters*, vol. 43, pp. 1973 to 1976 (2002).

*Primary Examiner*—Taylor Victor Oh
(74) *Attorney, Agent, or Firm*—Wenderoth, Lind, & Ponack, L.L.P.

(57) ABSTRACT

The present invention relates to a novel malononitrile compound represented by the formula (A): wherein, $R_1$ represents C1 to C6 alkyl that may be substituted with halogen, C2 to C6 alkenyl that may be substituted with halogen, etc; $R_2$ represents hydrogen atom or C1 to C6 alkyl that may be substituted with halogen; $R_3$ represents hydrogen atom or C1 to C6 alkyl; $R_4$ represents hydrogen atom or C1 to C6 alkyl; $R_5$ represents C1 to C6 alkyl that may be substituted with halogen, C3 to C6 alkenyl that may be substituted with halogen, etc, or $R_4$ and $R_5$ may be combined at their terminal and represent ethylene that may be substituted with C1 to C3 alkyl or trimethylene that may be substituted with C1 to C3 alkyl; and $Z_1$ and $Z_2$, which are the same or different, represent oxygen atom or sulfur atom. The malononitrile compound has an efficient pesticidal activity and can control effectively pests such as insect pests, acarine pests, nematode pests and the like.

(A)

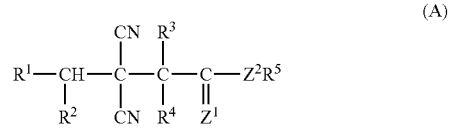

6 Claims, No Drawings

MALONONITRILE COMPOUND AND USE THEREOF

TECHNICAL FIELD

The present invention relates to malononitrile compounds and their use.

BACKGROUND ART

While various pesticide compositions have been used for the purpose of controlling pests such as insect pests, acarine pests, nematode pests and the like, sometimes the effect of those pesticide compositions is not always enough, and therefore the development of novel pesticide compositions having enough effect is desired.

It is an objective of the present invention to provide a method for controlling pests applying a novel compound having pesticidal activity and its effective dose to pests or their habitat.

DISCLOSURE OF INVENTION

The present inventors have intensively studied to find compounds having excellent pesticidal activity, and as a result, found out that the malononitrile compounds of formula (A) as depicted below have an excellent controlling activity for arthropod pests such as insect pests and acarine pests and pests such as nematode pests, thereby completing the present invention.

Namely, the present invention relates to a malononitrile compound represented by the formula (A) (hereinafter referred to as the present invention compound(s)):

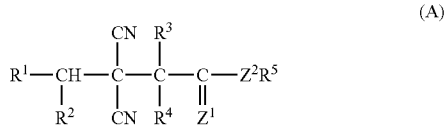

wherein, $R^1$ represents hydrogen atom, C1 to C6 alkyl that may be substituted with halogen, C2 to C6 alkenyl that may be substituted with halogen, C2 to C6 alkynyl that may be substituted with halogen, C3 to C6 cycloalkyl that may be substituted with halogen or C2 to C4 cyanoalkyl, $R^2$ represents hydrogen atom or C1 to C6 alkyl that may be substituted with halogen, $R^3$ represents hydrogen atom or C1 to C6 alkyl, $R^4$ represents hydrogen atom or C1 to C6 alkyl, $R^5$ represents C1 to C8 alkyl that may be substituted with halogen, C3 to C8 alkenyl that may be substituted with halogen, C3 to C8 alkynyl that may be substituted with halogen, C3 to C6 cycloalkyl that may be substituted with halogen, C1 to C3 alkyl which is substituted with optionally halogenated C3 to C6 cycloalkyl, C2 to C8 cyanoalkyl or C3 to C8 alkoxyalkyl, or $R^4$ and $R^5$ may be combined at their terminal and represent ethylene that may be substituted with C1 to C3 alkyl or trimethylene that may be substituted with C1 to C3 alkyl, and $Z^1$ and $Z^2$, which are the same or different, each independently represent oxygen atom or sulfur atom;

a pesticidal composition containing the present invention compound as active ingredient; and a method for controlling pests comprising applying an effective dose of the present invention compound to pests or habitat of pests.

MODE FOR CARRYING OUT THE INVENTION

In the present invention,

The notation of "C1 to C6 alkyl" means alkyl whose total number of carbon atoms is 1 to 6. Similarly, "C2 to C4 cyanoalkyl" means that the total number of carbon atoms of cyanoalkyl is 2 to 4, that is, total carbon number is 2 to 4 including cyano bonded to alkyl.

The C1 to C6 alkyl that may be substituted with halogen represented by $R^1$ includes, for example, methyl, ethyl, propyl, isopropyl, butyl, isobutyl, sec-butyl, tert-butyl, pentyl, isopentyl, neopentyl, fluoromethyl, chloromethyl, trifluoromethyl, 2-fluoroethyl, 2-chloroethyl, 2,2,2-trifluoroethyl, pentafluoroethyl, 3-fluoropropyl, 3-chloropropyl, 3,3,3-trifluoropropyl, heptafluoropropyl and 2-chloro-1-methylethyl.

The C2 to C6 alkenyl that may be substituted with halogen represented by $R^1$ includes, for example, vinyl, allyl, 1-propenyl, 2-methyl-1-propenyl, 1-fluorovinyl, 2-fluorovinyl, 1-chlorovinyl, 2-chlorovinyl, 2,2-difluorovinyl, 2,2-dichlorovinyl, 2,2-dibromovinyl, 3,3,3-trifluoro-1-propenyl and 2,3,3-trifluoro-2-propenyl.

The C2 to C6 alkynyl that may be substituted with halogen represented by $R^1$ includes, for example, ethynyl, 1-propynyl, 4,4,4-trifluoro-2-butynyl and 3-chloro-2-propynyl.

The C3 to C6 cycloalkyl that may be substituted with halogen represented by $R^1$ includes, for example, cyclopropyl, cyclobutyl, cyclopentyl, cyclohexyl 2,2-dichlorocyclopropyl and 2,2,3,3-tetrafluorocyclopropyl.

The C2 to C4 cyanoalkyl represented by $R^1$ includes, for example, cyanomethyl, 1-cyanoethyl and 2-cyanoethyl.

The C1 to C6 alkyl that may be substituted with halogen represented by $R^2$ includes, for example, methyl, ethyl and propyl.

The C1 to C6 alkyl represented by $R^3$ includes, for example, methyl, ethyl, propyl, butyl, pentyl, hexyl, isopropyl, tert-butyl and isobutyl.

The C1 to C6 alkyl represented by $R^4$ includes, for example, methyl, ethyl, propyl, butyl, pentyl, hexyl, isopropyl, tert-butyl and isobutyl.

The C1 to C8 alkyl that may be substituted with halogen represented by $R^5$ is preferably C2 to C6 alkyl that may be substituted with halogen, and such C2 to C6 alkyl that may be substituted with halogen includes, for example, ethyl, 2-chloroethyl, 2,2,2-trifluoroethyl, propyl, isopropyl, 2-chloro-1-methylethyl, 3-chloropropyl, 2,2,2-trifluoro-1-(trifluoromethyl)ethyl, butyl, isobutyl, sec-butyl, tert-butyl, pentyl, neopentyl, tert-pentyl, 1,2-dimethylpropyl, 1,3-dimethylbutyl and hexyl.

The C3 to C8 alkenyl that may be substituted with halogen represented by $R^5$ is preferably C3 to C6 alkenyl that may be substituted with halogen, and such C3 to C6 alkenyl that may be substituted with halogen includes, for example, allyl, 2-butenyl, 3-butenyl, 2-methyl-2-propenyl, 1,1-dimethyl-2-propenyl and 3-methyl-2-butenyl.

The C3 to C8 alkynyl that may be substituted with halogen represented by $R^5$ is preferably C3 to C6 alkynyl that may be substituted with halogen, and such C3 to C6 alkynyl that may be substituted with halogen includes, for example, 2-propynyl, 2-butynyl, 1,1-dimethyl-2-propynyl, 1-methyl-2-ethyl-2-propynyl and 3-butynyl.

The C3 to C6 cycloalkyl that may be substituted with halogen represented by $R^5$ includes, for example, cyclopropyl, cyclobutyl, cyclopentyl and cyclohexyl.

The C1 to C3 alkyl which is substituted with optionally halogenated C3 to C6 cycloalkyl represented by $R^5$ includes, for example, cyclopropylmethyl, cyclobutylmethyl, cyclopentylmethyl and cyclohexylmethyl.

The C2 to C8 cyanoalkyl represented by $R^5$ includes, for example, cyanomethyl, 1-cyanoethyl, 2-cyanoethyl and 1-cyano-1-methylethyl.

The C3 to C8 alkoxyalkyl represented by $R^5$ includes, for example, 2-methoxyethyl, 3-methoxypropyl, 3-ethoxypropyl and 3-methoxy-3-methylbutyl.

In case that $R^4$ and $R^5$ is combined at their terminal, the ethylene that may be substituted with C1 to C3 alkyl includes, for example, ethylene and propylene, and the trimethylene that may be substituted with C1 to C3 alkyl includes, for example, trimethylene.

As the aspects of the present invention compound, for example, the following compounds are exemplified.

a malononitrile compound wherein $R^3$ is hydrogen atom in the formula (A);

a malononitrile compound wherein $R^3$ and $R^4$ are hydrogen atoms in the formula (A);

a malononitrile compound wherein $R^2$ is hydrogen atom in the formula (A);

a malononitrile compound wherein $R^2$ and $R^3$ are hydrogen atoms in the formula (A);

a malononitrile compound wherein $R^2$, $R^3$ and $R^4$ are hydrogen atoms in the formula (A);

a malononitrile compound wherein $R^1$ is C1 to C6 alkyl that may be substituted with halogen, C2 to C6 alkenyl that may be substituted with halogen, C2 to C6 alkynyl that may be substituted with halogen, C3 to C6 cycloalkyl that may be substituted with halogen or C2 to C4 cyanoalkyl in the formula (A);

a malononitrile compound wherein $R^1$ is C1 to C3 alkyl in the formula (A);

a malononitrile compound wherein $R^1$ is C1 to C3 haloalkyl in the formula (A);

a malononitrile compound wherein $R^1$ is C2 to C4 alkenyl in the formula (A);

a malononitrile compound wherein $R^1$ is C2 to C4 haloalkenyl in the formula (A);

a malononitrile compound wherein $R^1$ is C3 to C6 cycloalkyl in the formula (A);

a malononitrile compound wherein $R^1$ is C3 to C6 halocycloalkyl in the formula (A);

a malononitrile compound wherein $R^1$ is ethyl in the formula (A);

a malononitrile compound wherein $R^1$ is propyl in the formula (A);

a malononitrile compound wherein $R^1$ is 2,2,2-trifluoroethyl in the formula (A);

a malononitrile compound wherein $R^1$ is vinyl in the formula (A);

a malononitrile compound wherein $R^1$ is 2-methyl-1-propenyl in the formula (A);

a malononitrile compound wherein $R^1$ is 1-propenyl in the formula (A);

a malononitrile compound wherein $R^1$ is 2,3,3-trifluoro-2-propenyl in the formula (A);

a malononitrile compound wherein $R^1$ is cyclopropyl in the formula (A);

a malononitrile compound wherein $R^1$ is 2,2-dichloro-1-cyclopropyl in the formula (A);

a malononitrile compound wherein $R^1$ is C1 to C6 alkyl that may be substituted with halogen, C2 to C6 alkenyl that may be substituted with halogen, C2 to C6 alkynyl that may be substituted with halogen, C3 to C6 cycloalkyl that may be substituted with halogen or C2 to C4 cyanoalkyl, and $R^3$ is hydrogen atom in the formula (A);

a malononitrile compound wherein $R^1$ is C1 to C3 alkyl and $R^3$ is hydrogen atom in the formula (A);

a malononitrile compound wherein $R^1$ is C1 to C3 haloalkyl and $R^3$ is hydrogen atom in the formula (A);

a malononitrile compound wherein $R^1$ is C2 to C4 alkenyl and $R^3$ is hydrogen atom in the formula (A);

a malononitrile compound wherein $R^1$ is C2 to C4 haloalkenyl and $R^3$ is hydrogen atom in the formula (A);

a malononitrile compound wherein $R^1$ is C3 to C6 cycloalkyl and $R^3$ is hydrogen atom in the formula (A);

a malononitrile compound wherein $R^1$ is C3 to C6 halocycloalkyl and $R^3$ is hydrogen atom in the formula (A);

a malononitrile compound wherein $R^1$ is C1 to C6 alkyl that may be substituted with halogen, C2 to C6 alkenyl that may be substituted with halogen, C2 to C6 alkynyl that may be substituted with halogen, C3 to C6 cycloalkyl that may be substituted with halogen or C2 to C4 cyanoalkyl, and $R^3$ and $R^4$ are hydrogen atoms in the formula (A);

a malononitrile compound wherein $R^1$ is C1 to C3 alkyl, and $R^3$ and $R^4$ are hydrogen atoms in the formula (A);

a malononitrile compound wherein $R^1$ is C1 to C3 haloalkyl, and $R^3$ and $R^4$ are hydrogen atoms in the formula (A);

a malononitrile compound wherein $R^1$ is C2 to C4 alkenyl, and $R^3$ and $R^4$ are hydrogen atoms in the formula (A);

a malononitrile compound wherein $R^1$ is C2 to C4 haloalkenyl, and $R^3$ and $R^4$ are hydrogen atoms in the formula (A);

a malononitrile compound wherein $R^1$ is C3 to C6 cycloalkyl, and $R^3$ and $R^4$ are hydrogen atoms in the formula (A);

a malononitrile compound wherein $R^1$ is C3 to C6 halocycloalkyl, and $R^3$ and $R^4$ are hydrogen atoms in the formula (A);

a malononitrile compound wherein $R^1$ is C1 to C6 alkyl that may be substituted with halogen, C2 to C6 alkenyl that may be substituted with halogen, C2 to C6 alkynyl that may be substituted with halogen, C3 to C6 cycloalkyl that may be substituted with halogen or C2 to C4 cyanoalkyl, and $R^2$ is hydrogen atom in the formula (A);

a malononitrile compound wherein $R^1$ is C1 to C3 alkyl, and $R^2$ is hydrogen atom in the formula (A);

a malononitrile compound wherein $R^1$ is C1 to C3 haloalkyl, and $R^2$ is hydrogen atom in the formula (A);

a malononitrile compound wherein $R^1$ is C2 to C4 alkenyl, and $R^2$ is hydrogen atom in the formula (A);

a malononitrile compound wherein $R^1$ is C2 to C4 haloalkenyl, and $R^2$ is hydrogen atom in the formula (A);

a malononitrile compound wherein $R^1$ is C3 to C6 cycloalkyl, and $R^2$ is hydrogen atom in the formula (A);

a malononitrile compound wherein $R^1$ is C3 to C6 halocycloalkyl, and $R^2$ is hydrogen atom in the formula (A);

a malononitrile compound wherein $R^1$ is C1 to C6 alkyl that may be substituted with halogen, C2 to C6 alkenyl that may be substituted with halogen, C2 to C6 alkynyl that may be substituted with halogen, C3 to C6 cycloalkyl that may be substituted with halogen or C2 to C4 cyanoalkyl, and $R^2$ and $R^3$ are hydrogen atoms in the formula (A);

a malononitrile compound wherein $R^1$ is C1 to C3 alkyl, and $R^2$ and $R^3$ are hydrogen atoms in the formula (A);

a malononitrile compound wherein $R^1$ is C1 to C3 haloalkyl, and $R^2$ and $R^3$ are hydrogen atoms in the formula (A);

a malononitrile compound wherein $R^1$ is C2 to C4 alkenyl, and $R^2$ and $R^3$ are hydrogen atoms in the formula (A);

a malononitrile compound wherein $R^1$ is C2 to C4 haloalkenyl, and $R^2$ and $R^3$ are hydrogen atoms in the formula (A);

a malononitrile compound wherein $R^1$ is C3 to C6 cycloalkyl, and $R^2$ and $R^3$ are hydrogen atoms in the formula (A);

a malononitrile compound wherein $R^1$ is C3 to C6 halocycloalkyl, and $R^2$ and $R^3$ are hydrogen atoms in the formula (A);

a malononitrile compound wherein $R^1$ is C1 to C6 alkyl that may be substituted with halogen, C2 to C6 alkenyl that may be substituted with halogen, C2 to C6 alkynyl that may be substituted with halogen, C3 to C6 cycloalkyl that may be substituted with halogen or C2 to C4 cyanoalkyl, and $R^2$, $R^3$ and $R^4$ are hydrogen atoms in the formula (A);

a malononitrile compound wherein $R^1$ is C1 to C3 alkyl, and $R^2$, $R^3$ and R are hydrogen atoms in the formula (A);

a malononitrile compound wherein $R^1$ is C1 to C3 haloalkyl, and $R^2$, $R^3$ and $R^4$ are hydrogen atoms in the formula (A);

a malononitrile compound wherein $R^1$ is C2 to C4 alkenyl, and $R^2$, $R^3$ and $R^4$ are hydrogen atoms in the formula (A);

a malononitrile compound wherein $R^1$ is C2 to C4 haloalkenyl, and $R^2$, $R^3$ and $R^4$ are hydrogen atoms in the formula (A);

a malononitrile compound wherein $R^1$ is C3 to C6 cycloalkyl, and $R^2$, $R^3$ and $R^4$ are hydrogen atoms in the formula (A);

a malononitrile compound wherein $R^1$ is C3 to C6 halocycloalkyl, and $R^2$, $R^3$ and $R^4$ are hydrogen atoms in the formula (A);

a malononitrile compound wherein $R^1$ is ethyl, and $R^3$ is hydrogen atom in the formula (A);

a malononitrile compound wherein $R^1$ is propyl, and $R^3$ is hydrogen atom in the formula (A);

a malononitrile compound wherein $R^1$ is 2,2,2-trifluoroethyl, and $R^3$ is hydrogen atom in the formula (A);

a malononitrile compound wherein $R^1$ is vinyl, and $R^3$ is hydrogen atom in the formula (A);

a malononitrile compound wherein $R^1$ is 2-methyl-1-propenyl, and $R^3$ is hydrogen atom in the formula (A);

a malononitrile compound wherein $R^1$ is 1-propenyl, and $R^3$ is hydrogen atom in the formula (A);

a malononitrile compound wherein $R^1$ is 2,3,3-trifluoro-2-propenyl, and $R^3$ is hydrogen atom in the formula (A);

a malononitrile compound wherein $R^1$ is cyclopropyl, and $R^3$ is hydrogen atom in the formula (A);

a malononitrile compound wherein $R^1$ is 2,2-dichloro-1-cyclopropyl, and $R^3$ is hydrogen atom in the formula (A);

a malononitrile compound wherein $R^1$ is ethyl, and $R^3$ and $R^4$ are hydrogen atoms in the formula (A);

a malononitrile compound wherein $R^1$ is propyl, and $R^3$ and $R^4$ are hydrogen atoms in the formula (A);

a malononitrile compound wherein $R^1$ is 2,2,2-trifluoroethyl, and $R^3$ and $R^4$ are hydrogen atoms in the formula (A);

a malononitrile compound wherein $R^1$ is vinyl, and $R^3$ and $R^4$ are hydrogen atoms in the formula (A);

a malononitrile compound wherein $R^1$ is 2-methyl-1-propenyl, and $R^3$ and $R^4$ are hydrogen atoms in the formula (A);

a malononitrile compound wherein $R^1$ is 1-propenyl, and $R^3$ and $R^4$ are hydrogen atoms in the formula (A);

a malononitrile compound wherein $R^1$ is 2,3,3-trifluoro-2-propenyl, and $R^3$ and $R^4$ are hydrogen atoms in the formula (A);

a malononitrile compound wherein $R^1$ is cyclopropyl, and $R^3$ and $R^4$ are hydrogen atoms in the formula (A);

a malononitrile compound wherein $R^1$ is 2,2-dichloro-1-cyclopropyl, and $R^3$ and $R^4$ are hydrogen atoms in the formula (A);

a malononitrile compound wherein $R^1$ is ethyl, and $R^2$ is hydrogen atom in the formula (A);

a malononitrile compound wherein $R^1$ is propyl, and $R^2$ is hydrogen atom in the formula (A);

a malononitrile compound wherein $R^1$ is 2,2,2-trifluoroethyl, and $R^2$ is hydrogen atom in the formula (A);

a malononitrile compound wherein $R^1$ is vinyl, and $R^2$ is hydrogen atom in the formula (A);

a malononitrile compound wherein $R^1$ is 2-methyl-1-propenyl, and $R^2$ is hydrogen atom in the formula (A);

a malononitrile compound wherein $R^1$ is 1-propenyl, and $R^2$ is hydrogen atom in the formula (A);

a malononitrile compound wherein $R^1$ is 2,3,3-trifluoro-2-propenyl, and $R^2$ is hydrogen atom in the formula (A);

a malononitrile compound wherein $R^1$ is cyclopropyl, and $R^2$ is hydrogen atom in the formula (A);

a malononitrile compound wherein $R^1$ is 2,2-dichloro-1-cyclopropyl, and $R^2$ is hydrogen atom in the formula (A);

a malononitrile compound wherein $R^1$ is ethyl, and $R^2$ and $R^3$ are hydrogen atoms in the formula (A);

a malononitrile compound wherein $R^1$ is propyl, and $R^2$ and $R^3$ are hydrogen atoms in the formula (A);

a malononitrile compound wherein $R^1$ is 2,2,2-trifluoroethyl, and $R^2$ and $R^3$ are hydrogen atoms in the formula (A);

a malononitrile compound wherein $R^1$ is vinyl, and $R^2$ and $R^3$ are hydrogen atoms in the formula (A);

a malononitrile compound wherein $R^1$ is 2-methyl-1-propenyl, and $R^2$ and $R^3$ are hydrogen atoms in the formula (A);

a malononitrile compound wherein $R^1$ is 1-propenyl, and $R^2$ and $R^3$ are hydrogen atoms in the formula (A);

a malononitrile compound wherein $R^1$ is 2,3,3-trifluoro-2-propenyl, and $R^2$ and $R^3$ are hydrogen atoms in the formula (A);

a malononitrile compound wherein $R^1$ is cyclopropyl, and $R^2$ and $R^3$ are hydrogen atoms in the formula (A);

a malononitrile compound wherein $R^1$ is 2,2-dichloro-1-cyclopropyl, and $R^2$ and $R^3$ are hydrogen atoms in the formula (A);

a malononitrile compound wherein $R^1$ is ethyl, and $R^2$, $R^3$ and $R^4$ are hydrogen atoms in the formula (A);

a malononitrile compound wherein $R^1$ is propyl, and $R^2$, $R^3$ and $R^4$ are hydrogen atoms in the formula (A);

a malononitrile compound wherein $R^1$ is 2,2,2-trifluoroethyl, and $R^2$, $R^3$ and $R^4$ are hydrogen atoms in the formula (A);

a malononitrile compound wherein $R^1$ is vinyl, and $R^2$, $R^3$ and $R^4$ are hydrogen atoms in the formula (A);

a malononitrile compound wherein $R^1$ is 2-methyl-1-propenyl, and $R^2$, $R^3$ and $R^4$ are hydrogen atoms in the formula (A);

a malononitrile compound wherein $R^1$ is 1-propenyl, and $R^2$, $R^3$ and $R^4$ are hydrogen atoms in the formula (A);

a malononitrile compound wherein $R^1$ is 2,3,3-trifluoro-2-propenyl, and $R^2$, $R^3$ and $R^4$ are hydrogen atoms in the formula (A);

a malononitrile compound wherein $R^1$ is cyclopropyl, and $R^2$, $R^3$ and $R^4$ are hydrogen atoms in the formula (A);

a malononitrile compound wherein $R^1$ is 2,2-dichloro-1-cyclopropyl, and $R^2$, $R^3$ and $R^4$ are hydrogen atoms in the formula (A);

a malononitrile compound wherein $R^4$ is hydrogen atom or C1 to C6 alkyl, $R^5$ is C1 to C6 alkyl that may be substituted with halogen, C3 to C6 alkenyl that may be substituted with halogen, C3 to C6 alkynyl that may be substituted with halogen, C3 to C6 cycloalkyl that may be substituted with halogen or C1 to C3 alkyl which is substituted with optionally halogenated C3 to C6 cycloalkyl, or $R^4$ and $R^5$ which are combined at their terminal is ethylene that may be substituted with C1 to C3 alkyl or trimethylene that may be substituted with C1 to C3 alkyl in the formula (A);

a malononitrile compound wherein $R^5$ is C1 to C6 alkyl that may be substituted with halogen, C3 to C6 alkenyl that may be substituted with halogen, C3 to C6 alkynyl that may be substituted with halogen, C3 to C6 cycloalkyl that may be substituted with halogen or C1 to C3 alkyl which is substituted with optionally halogenated C3 to C6 cycloalkyl in the formula (A);

a malononitrile compound wherein $R^5$ is C1 to C6 alkyl that may be substituted with halogen in the formula (A);

a malononitrile compound wherein $R^5$ is C1 to C6 alkyl that may be substituted with halogen, and $Z^1$ and $Z^2$ are oxygen atoms in the formula (A);

a malononitrile compound wherein $R^4$ and $R^5$ which are combined at their terminal is ethylene that may be substituted with C1 to C3 alkyl in the formula (A);

a malononitrile compound wherein $R^4$ and $R^5$ which are combined at their terminal is ethylene that may be substituted with C1 to C3 alkyl, and $Z^1$ and $Z^2$ are oxygen atoms in the formula (A);

The following will describe a production process for the present invention compounds.

The present invention compounds can be produced, for example, according to the following (Production Process 1) to (Production Process 3).

(Production Process 1)

The present invention compounds can be produced by reacting compound (a) and compound (b).

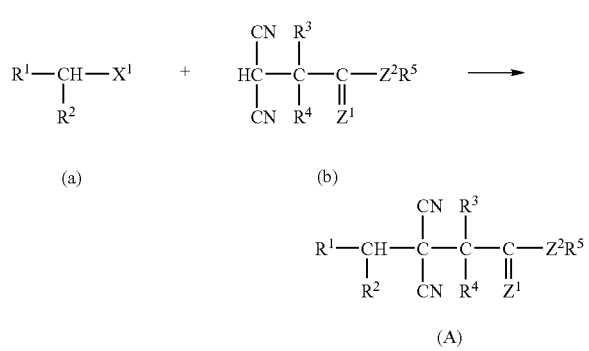

wherein, $X^1$ represents chlorine, bromine, iodine or methanesulfonyloxy, and $R^1$ to $R^5$, $Z^1$ and $Z^2$ are as defined above.

The reaction is generally carried out in the presence of base in a solvent.

The solvent to be used in the reaction includes, for example, aliphatic hydrocarbons such as hexane, heptane, octane, cyclohexane and the like, aromatic hydrocarbons such as toluene, xylene, mesitylene and the like, ethers such as diethyl ether, methyl tert-butyl ether, tetrahydrofuran, 1,4-dioxane and the like, acid amides such as N,N-dimethylformamide and the like, dialkylsulfoxides such as dimethylsulfoxide and the like, and mixtures thereof.

The base to be used in the reaction includes, for example, carbonates such as sodium carbonate, potassium carbonate and the like, alkali metal hydrides such as sodium hydride and the like, and tertiary amines such as triethylamine, diisopropylethylamine and the like.

The amount of compound (a) to be used in the reaction is usually 1 to 10 moles relative to 1 mole of compound (b), and the amount of the base is usually 1 to 10 moles relative to 1 mole of compound (b).

The reaction temperature is usually in the range of –20° C. to 100° C., and the reaction time is usually in the range of 0.1 to 24 hours.

After completion of the reaction, the present invention compound can be isolated by subjecting the reaction mixture to ordinary post-treatment such as adding the reaction mixture into water, extracting with an organic solvent, concentrating and drying the organic phase obtained and the like. The isolated present invention compound can be purified by a technique such as chromatography, recrystallization and the like, if necessary.

(Production Process 2)

The present invention compounds can be produced by reacting compound (c) and compound (d).

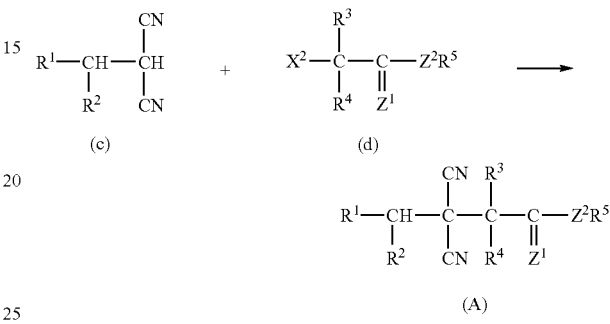

wherein, $X^2$ represents chlorine, bromine, iodine or methanesulfonyloxy, and $R^1$ to $R^5$, $Z^1$ and $Z^2$ are as defined above.

The reaction is generally carried out in the presence of base in a solvent.

The solvent to be used in the reaction includes, for example, aliphatic hydrocarbons such as hexane, heptane, octane, cyclohexane and the like, aromatic hydrocarbons such as toluene, xylene, mesitylene and the like, ethers such as diethyl ether, methyl tert-butyl ether, tetrahydrofuran, 1,4-dioxane and the like, acid amides such as N,N-dimethylformamide and the like, dialkylsulfoxides such as dimethylsulfoxide and the like, and mixtures thereof.

The base to be used in the reaction includes, for example, carbonates such as sodium carbonate, potassium carbonate and the like, alkali metal hydrides such as sodium hydride and the like, and tertiary amines such as triethylamine, diisopropylethylamine and the like.

The amount of compound (d) to be used in the reaction is usually 1 to 10 moles relative to 1 mole of compound (c), and the amount of the base is usually 1 to 10 moles relative to 1 mole of compound (c).

The reaction temperature is usually in the range of –20° C. to 100° C., and the reaction time is usually in the range of 0.1 to 24 hours.

After completion of the reaction, the present invention compound represented by the formula (A) can be isolated by subjecting the reaction mixture to ordinary post-treatment such as adding the reaction mixture into water, extracting with an organic solvent, concentrating and drying the organic phase obtained and the like. The isolated present invention compound represented by the formula (A) can be purified by a technique such as chromatography, recrystallization and the like, if necessary.

(Production Process 3)

Among the present invention compounds, the compound (A-1) wherein $Z^1$ and $Z^2$ are oxygen atoms can be also produced by reacting compound (e) and trifluoracetic acid (first step), and then reacting the obtained compound (f) and alcoholic compound represented by the formula: $R^5OH$ (second step).

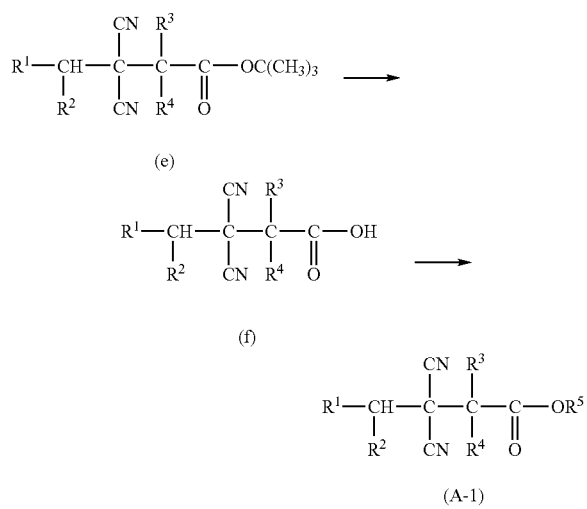

(First Step)

The reaction of first step can be carried out, for example, by mixing compound (e) with trifluoracetic acid.

The amount of trifluoracetic acid being used in the reaction is usually 1 to 50 moles relative to 1 mole of compound (e).

The reaction temperature is usually in the range of 0° C. to 70° C., and the reaction time is usually in the range of 0.1 to 24 hours.

After completion of the reaction, the reaction mixture can be concentrated directly, and if necessary, an organic solvent such as toluene and the like is added to the residue, followed by re-concentration, and then the obtained residue can be subjected to the second step.

(Second Step)

The reaction of second step can be carried out by reacting compound (f) obtained in the first step with an alcoholic compound represented by the formula: $R^5OH$.

The reaction is usually carried out using further triphenylphosphine and dialkyl azodicarboxylate (diisopropyl azodicarboxylate etc.)

The reaction is generally carried out in a solvent. The solvent being used in the reaction include, for example, aliphatic hydrocarbons such as hexane, heptane, octane and the like, aromatic hydrocarbons such as toluene, xylene, mesitylene and the like, esters such as ethyl acetate, butyl acetate and the like, and mixtures thereof.

The amount of triphenylphosphine being used in the reaction is usually 1 to 5 moles relative to 1 mole of compound (e) which is used in the first step, the amount of dialkyl azodicarboxylate is usually 1 to 2 moles relative to 1 mole of compound (e), and the amount of alcoholic compound represented by the formula: $R^5OH$ is usually 1 to 10 moles relative to 1 mole of compound (e).

The reaction temperature is usually in the range of −20° C. to 100° C., and the reaction time is usually in the range of 0.1 to 24 hours.

After completion of the reaction, the compound (A-1) can be isolated by subjecting the reaction mixture to ordinary post-treatment such as filtrating after addition of aliphatic hydrocarbons such as hexane etc. to the reaction mixture, concentrating the filtrate if required, followed by subjecting to silica gel chromatography and the like.

The compound (e) that is a raw material compound in (Production Process 3) can be produced, for example, according to (Production Process 1) or (Production Process 2).

The following will describe a production of the production intermediate of the present invention compounds.

The compound (b) can be produced, for example, by reacting compound (d) with malononitrile.

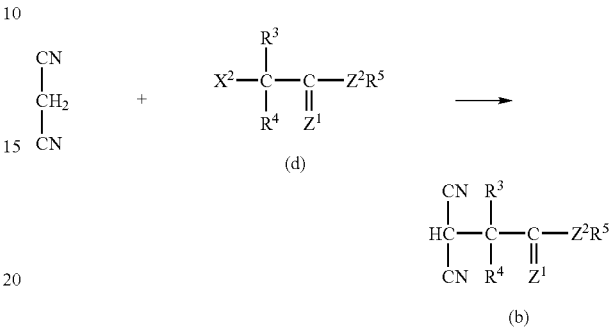

wherein, $R^3$ to $R^5$, $Z^1$, $Z^2$ and $X^2$ are as defined above.

The reaction is generally carried out in the presence of base in a solvent.

The solvent to be used in the reaction includes, for example, aliphatic hydrocarbons such as hexane, heptane, octane, cyclohexane and the like, aromatic hydrocarbons such as toluene, xylene, mesitylene and the like, ethers such as diethyl ether, methyl tert-butyl ether, tetrahydrofuran, 1,4-dioxane and the like, acid amides such as N,N-dimethylformamide and the like, dialkylsulfoxides such as dimethylsulfoxide and the like, and mixtures thereof.

The base to be used in the reaction includes, for example, carbonates such as sodium carbonate, potassium carbonate and the like, alkali metal hydrides such as sodium hydride and the like, and tertiary amines such as triethylamine, diisopropylethylamine and the like.

The amount of compound (d) to be used in the reaction is usually 0.2 to 1 moles relative to 1 mole of malononitrile, and the amount of the base is usually 1 to 10 moles relative to 1 mole of malononitrile.

The reaction temperature is usually in the range of −20° C. to 100° C., and the reaction time is usually in the range of 0.1 to 24 hours.

After completion of the reaction, the compound (b) can be isolated by subjecting the reaction mixture to ordinary post-treatment such as adding the reaction mixture into water, extracting with an organic solvent, concentrating and drying the obtained organic phase and the like. The isolated compound (b) can be purified by a technique such as chromatography, recrystallization and the like, if necessary.

The compound (c) can be produced, for example, by reacting compound (a) with malononitrile.

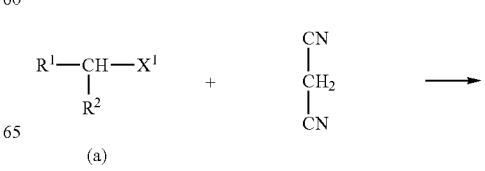

-continued

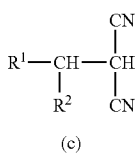

(c)

wherein, $R^1$, $R^2$ and $X^1$ are as defined above.

The reaction is generally carried out in the presence of base in a solvent.

The solvent to be used in the reaction includes, for example, aliphatic hydrocarbons such as hexane, heptane, octane, cyclohexane and the like, aromatic hydrocarbons such as toluene, xylene, mesitylene and the like, ethers such as diethyl ether, methyl tert-butyl ether, tetrahydrofuran, 1,4-dioxane and the like, acid amides such as N,N-dimethylformamide and the like, and mixtures thereof.

The base to be used in the reaction includes, for example, carbonates such as sodium carbonate, potassium carbonate and the like, alkali metal hydrides such as sodium hydride and the like, and tertiary amines such as triethylamine, diisopropylethylamine and the like.

The amount of compound (a) to be used in the reaction is usually 0.2 to 1 moles relative to 1 mole of malononitrile, and the amount of the base is usually 1 to 10 moles relative to 1 mole of malononitrile.

The reaction temperature is usually in the range of −20° C. to 100° C., and the reaction time is usually in the range of 0.1 to 24 hours.

After completion of the reaction, the compound (c) can be isolated by subjecting the reaction mixture to ordinary post-treatment such as adding the reaction mixture into water, extracting with an organic solvent, concentrating and drying the obtained organic phase and the like. The isolated compound (c) can be purified by a technique such as chromatography, recrystallization and the like, if necessary.

In addition, the compound (c) can be produced according to the method described in J. Chem. Soc. Perkin Trans., 1, 2589-2592 (1991).

The pests against which the present invention compound has control activity may include, for example, arthropods such as insect pests and acarine pests and the like, and nematode pests. Specific examples are listed below:

Hemiptera:

Delphacidae such as *Laodelphax striatellus, Nilaparvata lugens, Sogatella furcifera* and the like, Deltocephalidae such as *Nephotettix cincticeps, Nephotettix virescens* and the like, Aphididae such as *Aphis gossypii, Myzus persicae* and the like, Pentatomidae such as *Nezara antennata, Riptortus clavetus, Eysarcoris lewisi, Eysarcoris parvus, Plautia stali, Halyomorpha mista* and the like, Aleyrodidae such as *Trialeurodes vaporariorum, Bemisia argentifolii* and the like, Coccidae such as *Aonidiella aurantii, Comstockaspis perniciosa, Unaspis citri, Ceroplastes rubens, Icerya purchasi* and the like, Tingidae, Psyllidae, and the like;

Lepidoptera:

Pyralidae such as *Chilo suppressalis, Cnaphalocrocis medinalis, Notarcha derogata, Plodia interpunctella* and the like, Noctuidae such as *Spodoptera litura, Pseudaletia separata, Thoricoplusia* spp., *Heliothis* spp., *Helicoverpa* spp. and the like, Pieridae such as *Pieris rapae* and the like, Tortricidae such as *Adoxophyes* spp., *Grapholita molesta, Cydia pomonella* and the like, Carposimidae such as *Carposina niponensis* and the like, Lyonetiidae such as *Lyonetia* spp. and the like, Lymantriidae such as *Lymantria* spp., *Euproctis* spp., and the like, Yponomeutidae such as *Plutella xylostella* and the like, Gelechiidae such as *Pectinophora gossypiella* and the like, Arctiidae such as *Hyphantria cunea* and the like, Tineidae such as *Tinea translucens, Tineola bisselliella* and the like;

Diptera:

Calicidae such as *Culex pipiens pallens, Culex tritaeniorhynchus, Culex quinquefasciatus* and the like,

*Aedes* spp. such as *Aedes aegypti, Aedes albopictus* and the like,

*Anopheles* spp. such as *Anopheles sinensis* and the like,

Chironomidae,

Muscidae such as *Musca domestica, Muscina stabulans* and the like,

Calliphoridae,

Sarcophagidae,

Fanniidae,

Anthomyiidae such as *Delia platura, Delia antiqua* and the like,

Tephritidae,

Drosophilidae,

Psychodidae,

Tabanidae,

Simuliidae,

Stomoxyidae,

Agromyzidae, and the like;

Coleoptera:

*Diabrotica* spp. such as *Diabrotica virgifera virgifera, Diabrotica undecimpunctata howardi* and the like, Scarabaeidae such as *Anomala cuprea, Anomala rufocuprea* and the like, Curculionidae such as *Sitophilus zeamais, Lissorhoptrus oryzophilus, Callosobruchuys chienensis* and the like, Tenebrionidae such as *Tenebrio molitor, Tribolium castaneum* and the like, Chrysomelidae such as *Oulema oryzae, Aulacophora femoralis, Phyllotreta striolata, Leptinotarsa decemlineata* and the like, Anobiidae,

*Epilachna* spp. such as *Epilachna vigintioctopunctata* and the like,

Lyctidae,

Bostrychidae,

Cerambycidae,

*Paederus fuscipes*;

Blattodea: *Blattella germanica, Periplaneta fuliginosa, Periplaneta americana, Periplaneta brunnea, Blatta orientalis* and the like;

Thysanoptera: *Thrips palmi, Thrips tabaci, Frankliniella occidentalis, Frankliniella intonsa* and the like;

Hymenoptera: Formicidae, Vespidae, bethylid wasp, Tenthredimidae such as *Athalia japonica*, and the like;

Orthoptera: Gryllotalpidae, Acrididae, and the like;

Aphaniptera: *Ctenocephalides felis, Ctenocephalides canis, Pulex irritans, Xenopsylla cheopis*, and the like;

Anoplura: *Pediculus humanus corporis, Phthirus pubis, Haematopinus eurysternus, Dalmalinia ovis*, and the like;

Isoptera: *Reticulitermes speratus, Coptotermes formosanus*, and the like;

Acarina:

Tetranychidae such as *Tetranychus urticae, Tetranychus kanzawai, Panonychus citri, Panonychus ulmi, Oligonychus* spp., and the like, Eriophyidae such as *Aculops pelekassi, Aculus schlechtendali*, and the like, Tarsonemidae such as *Polyphagotarsonemus latus*, and the like, Tenuipalpidae, Tuckerellidae, Ixodidae such as *Haemaphysalis longicornis, Haemaphysalis flava, Dermacentor taiwanicus, Ixodes ovatus, Ixodes persulcatus, Boophilus microplus*, and the like, Acaridae such as *Tyrophagus putrescentiae*, and the like, Epidermoptidae such as *Dermatophagoides farinae, Dermatophagoides ptrenyssnus*, and the like, Cheyletidae such as *Cheyletus eruditus, Cheyletus malaccensis, Cheyletus moorei*, and the like, Dermanyssidae;

Araneae: *Chiracanthium japonicum, Latrodectus hasseltii*, and the like;

Chilopoda: *Thereuonema hilgendorfi, Scolopendra subspinipes*, and the like;

Diplopoda: *Oxidus gracilis, Nedyopus tambanus*, and the like;

Isopoda: *Armadillidium vulgare*, and the like;

Gastropoda: *Limax marginatus, Limax flavus*, and the like;

Nematoda: *Pratylenchus coffeae, Pratylenchus fallax, Heterodera glycines, Globodera rostochiensis, Meloidogyne hapla, Meloidogyne incognita*, and the like.

The pesticide composition of the present invention contains the present invention compound and an inert carrier. Generally, it is a preparation obtained by mixing the present invention compound and a carrier such as a solid carrier, a liquid carrier and a gaseous carrier, and if necessary, adding a surfactant and other adjuvant for formulation. The formulation includes, for example, an emulsion, an oil solution, a shampoo formulation, a flowable formulation, a powder, a wettable powder, a granule, a paste formulation, a microcapsule, a foam, an aerosol, a carbon dioxide gas formulation, a tablet, a resin formulation and the like. These formulations can be converted to use into a poison bait, a pesticide coil, an electric pesticide mat, a smoking agent, a fumigant or sheet.

In the pesticide composition of the present invention, the present invention compound is usually contained in an amount of 0.1% to 95% by weight.

The solid carrier for formulation includes, for example, a fine power and a granule of clays (e.g., kaolin clay, diatomite, bentonite, Fubasami clay, acid clay, etc.), synthetic hydrated silicon oxide, talc, ceramic, other inorganic minerals (e.g., sericite, quartz, sulfur, activated carbon, calcium carbonate, hydrated silica) or chemical fertilizers (e.g., ammonium sulfate, ammonium phosphate, ammonium nitrate, ammonium chloride, urea).

The liquid carrier for formulation includes, for example, aromatic or aliphatic hydrocarbons (e.g., xylene, toluene, alkylnaphthalene, phenylxylylethane, kerosine, light oil, hexane, cyclohexane), halogenated hydrocarbons (e.g., chlorobenzene, dichloromethane, dichloroethane, trichloroethane), alcohols (e.g., methanol, ethanol, isopropyl alcohol, butanol, hexanol, ethylene glycol), ethers (e.g., diethyl ether, ethylene glycol dimethyl ether, diethylene glycol monomethyl ether, diethylene glycol monoethyl ether, propylene glycol monomethyl ether, tetrahydrofuran, dioxane), esters (e.g., ethyl acetate, butyl acetate), ketones (e.g., acetone, methyl ethyl ketone, methyl isobutyl ketone, cyclohexanone), nitriles (e.g., acetonitrile, isobutyronitrile), sulfoxides (e.g., dimethylsulfoxide), acid amides (e.g., N,N-dimethylformamide, N,N-dimethylacetamide), vegetable oils (e.g., soy bean oil, cotton seed oil), vegetable essential oils (e.g., orange oil, hyssop oil, lemon oil) and water.

The gaseous carrier for formulation includes, for example, butane gas, chlorofluorocarbons, liquefied petroleum gas (LPG), dimethyl ether, carbon dioxide and the like.

The surfactant for formulation includes, for example, alkyl sulfate salts, alkylsulfonic acid salts, alkylarylsulfonic acid salts, alkyl aryl ethers and their polyoxyethylene derivatives, polyethylene glycol ethers, polyhydric alcohol esters, and sugar alcohol derivatives.

The other adjuvant for formulation includes, for example, binders, dispersants and stabilizers, and specifically for example, casein, gelatin, polysaccharides (e.g., starch, gum arabic, cellulose derivatives, alginic acid), lignin derivatives, bentonite, sugars, synthetic water-soluble polymers (e.g., polyvinyl alcohol, polyvinylpyrrolidone, polyacrylic acid), PAP (isopropyl acid phosphate), BHT (2,6-di-t-butyl-4-methylphenol), BHA (a mixture of 2-t-butyl-4-methoxyphenol and 3-t-butyl-4-methoxyphenol), vegetable oils, mineral oils, fatty acids, and fatty acid esters.

The base material for resin formulation includes, for example, polyvinyl chloride, polyurethane and the like. To these base materials, if necessary, a plasticizer such as phthalate (e.g., dimethyl phthalate, dioctyl phthalate), adipate and stearate may be added. The resin formulation can be obtained by kneading the compound into the base material using a known kneader and then molding by injection molding, extrusion molding, press molding and the like, and further, if necessary, via a process for cutting and the like, the resin formulation can be converted into a resin preparation such as board, film, tape, net, string and the like. These resin preparations can be converted into, for example, an animal collar, an animal ear tag, a sheet preparation, an attraction string, a gardening stick.

A base material for the poison bait includes, for example, grain powders, vegetable oils, sugars, and crystalline cellulose, and further, if necessary, antioxidants such as dibutylhydroxytoluene and nordihydroguaiaretic acid, preservatives such as dehydroacetic acid, agents for preventing children and pets from erroneously eating such as hot pepper powder, and pest-attractive flavors such as cheese flavor, onion flavor and peanut oil may be added to the base material.

Pests can be controlled by applying an effective dose of the present invention compound to pests directly and/or habitats of pests (e.g., plant, animal, soil). Usually the preparation of the pesticide composition of the present invention is used as the present invention compound.

When the pesticide composition of the present invention is used for a control of pests in agriculture and forestry, the application amount is usually 1 to 10,000 g/ha as an active ingredient. The emulsions, wettable powders, flowables and microcapsule formulations are usually applied after dilution with water to have an active ingredient concentration of 0.01 to 1000 ppm, while oil solution, powders and granules are usually applied as such. These preparations may be sprayed directly to the plant to be protected from pests. The pests living in a soil can be controlled by treating the soil with these preparations, and the preparations can also be applied to treat seedbeds prior to the planting plants or to treat planting holes or plant bottoms in the planting. Furthermore, the sheet preparation of the pesticide composition of the present invention can be applied by a method such as winding around plants, stretching in the vicinity of plants and laying on the soil surface at the plant bottom.

When the pesticide composition of the present invention is used for a control of pests in preventive measures, the application amount is usually 0.001 to 100 mg/m$^3$ as an active ingredient in case of application for open space, and 0.001 to 100 mg/m$^2$ as an active ingredient in case of application for plane surface. The emulsions, wettable powders and flowables are usually applied after dilution with water to have an active ingredient concentration of 0.01 to 10,000 ppm, while oil solutions, aerosols, smoking agents and poison baits are usually applied as such, and pesticide coils and electric pesticide mats are applied with emitting active ingredients by heating depending on their formulation form.

When the pesticide composition of the present invention is used for a control of parasite living outside of a livestock such as caw, horse, pig, sheep, goat and chicken, and a small animal such as dog, cat, rat and mouse, the pesticide composition can be applied to said animal by a veterinarily known method. Specifically, for systemic control, the pesticide composition is administered by means of, for example, a tablet, a mixture with feed, a suppository or an injection (e.g., intramuscular, subcutaneous, intravenous, intraperitoneal), and for non-systemic control, it is applied by a method such as spraying an oil solution or an aqueous liquid formulation, carrying out pour-on treatment or spot-on treatment, washing said animal with a shampoo formulation, attaching the resin formulation on said animal as a collar or an ear-tag, and the like. When the present invention compound is administered to an animal, its amount is usually in the range of 0.1 to 1,000 mg/kg body weight of the animal.

The pesticide composition of the present invention can also be used in admixture or combination with other insecticides, nematocides, acaricides, fungicides, herbicides, plant growth regulators, synergists, fertilizers, soil conditioners, animal feeds, and the like.

The active ingredients of such other insecticide and acaricide include, for example, pyrethroid compounds such as allethrin, tetramethrin, prallethrin, phenothrin, resmethrin, cyphenothrin, permethrin, cypermethrin, alpha-cypermethrin, zeta-cypermethrin, deltamethrin, tralomethrin, cyfluthrin, beta-cyfluthrin, cyhalothrin, lambda-cyhalothrin, flumethrin, imiprothrin, etofenprox, fenvalerate, esfenvalerate, fenpropathrin, silafluofen, bifenthrin, transfluthrin, flucythrinate, tau-fluvalinate, acrinathrin and tefluthrin; organophosphorus compounds such as dichlorvos, fenitrothion, cyanophos, profenofos, sulprofos, phenthoate, isoxathion, tetrachlorvinphos, fenthion, chlorpyriphos, diazinon, acephate, terbufos, phorate, chlorethoxyfos, fosthiazate, ethoprophos, cadusafos and methidathion; carbamate compounds such as propoxur, carbaryl, metoxadiazone, fenobucarb, methomyl, thiodicarb, alanycarb, benfuracarb, oxamyl, aldicarb and methiocarb; benzoylphenylurea compounds such as lufenuron, chlorfluazuron, hexaflumuron, diflubenzuron, triflumuron, teflubenzuron, flufenoxuron, fluazuron, novaluron and triazuron; juvenile hormone-like substances such as pyriproxyfen, methoprene, hydroprene and fenoxycarb; neonicotinoid compounds such as acetamiprid, nitenpyram, thiacloprid, thiamethoxam and dinotefuran; N-phenyl-pyrazole compounds such as acetoprole and ethiprole; benzoylhydrazine compounds such as tebufenozide, chromafenozide, methoxyfenozide and halofenozide; diafenthiuron; pymetrozine; flonicamid; triazamate; buprofezin; spinosad; emamectin benzoate; chlorfenapyr; indoxacarb MP; pyridalyl; cyromazine; fenpyroximate; tebufenpyrad; tolfenpyrad; pyridaben; pyrimidifen; fluacrypyrim; etoxazole; fenazaquin; acequinocyl; hexythiazox; clofentezine; fenbutatin oxide; dicofol, propargite; abamectin; milbemectin; amitraz; cartap; bensultap; thiocyclam; endosulfan; spirodiclofen; spiromesifen; and azadirachtin.

The active ingredients of such other fungicide include, for example, strobilurin compounds such as azoxystrobin; organophosphorus compounds such as tolclofos-methyl; azole compounds such as triflumizole, pefurazoate and difenoconazole; fthalide; flutolanil; validamycin; probenazole; diclomezine; pencycuron; dazomet; kasugamycin; IBP; pyroquilon; oxolinic acid; tricyclazole; ferimzone; mepronil; EDDP; isoprothiolane; carpropamid; diclocymet; furametpyr; fludioxonil; procymidone; and diethofencarb.

The present invention will be further illustrated by the following production examples, formulation examples, and test examples; however, the present invention is not limited to these examples. First, production examples of the present invention compounds are exemplified.

PRODUCTION EXAMPLE 1

(1) 1.4 g of sodium hydride (60% in oil) was suspended in 10 ml of N,N-dimethylformamide, and a solution of 3.35 g of 2-allylmalononitrile in 20 ml of N,N-dimethylformamide was added thereto at about 0° C. The solution was warmed to room temperature and N,N-dimethylformamide was added thereto to adjust total volume to 42 ml (hereinafter, thus obtained solution is referred to as solution A).

(2) 0.3 g of tert-butyl bromoacetate was dissolved in 1 ml of N,N-dimethylformamide and 1.5 ml of solution A was added thereto, and the reaction mixture was stirred for 4 hours at room temperature. Then, to the reaction mixture was added dilute hydrochloric acid, and extracted with ethyl acetate. The organic layer was washed successively with water and saturated brine, dried over anhydrous magnesium sulfate and concentrated under reduced pressure. The residue obtained was subjected to silica gel column chromatography to give 0.27 g of 2-(tert-butoxycarbonylmethyl)-2-allylmalononitrile (hereinafter referred to as the present invention compound (1)).

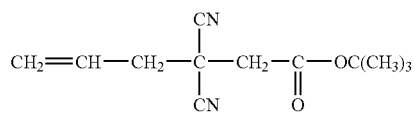

$^1$H-NMR (CDCl$_3$, TMS) δ (ppm): 1.53(9H, s), 2.79(2H, d), 2.86(2H, s), 5.39-5.48(2H, m), 5.82-5.98(1H, m)

PRODUCTION EXAMPLE 2

By using 0.27 g of ethyl 2-bromopropionate instead of tert-butyl bromoacetate according to Production Example 1 (2) was obtained 0.17 g of 2-[1-(ethoxycarbonyl)ethyl]-2-allylmalononitrile (hereinafter referred to as the present invention compound (2)).

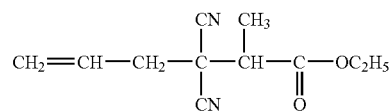

$^1$H-NMR (CDCl$_3$, TMS) δ (ppm): 1.33 (3H, t), 1.56 (3H, d), 2.74-2.84 (2H, m), 2.95 (1H, q), 4.26 (2H, q), 5.38-5.47 (2H, m), 5.85-5.98 (1H, m)

PRODUCTION EXAMPLE 3

By using 0.29 g of ethyl 2-bromobutyrate instead of tert-butyl bromoacetate according to Production Example 1 (2) was obtained 0.16 g of 2-[1-(ethoxycarbonyl)propyl]-2-allyl-malononitrile (hereinafter referred to as the present invention compound (3)).

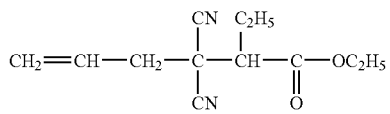

$^1$H-NMR (CDCl$_3$, TMS) δ (ppm): 1.06 (3H, t), 1.34 (3H, t), 1.92-2.09 (2H, m), 2.66-2.78 (3H, m), 4.30 (2H, q), 5.38-5.46 (2H, m), 5.84-5.98 (1H, m)

PRODUCTION EXAMPLE 4

By using 0.31 g of ethyl 2-bromovalerate instead of tert-butyl bromoacetate according to Production Example 1 (2) was obtained 0.16 g of 2-[1-(ethoxycarbonyl)butyl]-2-allyl-malononitrile (hereinafter referred to as the present invention compound (4)).

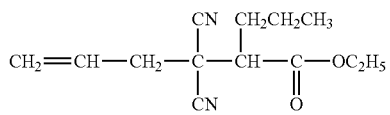

$^1$H-NMR (CDCl$_3$, TMS) δ (ppm): 0.99 (3H, t), 1.31 (3H, t), 1.36-1.50 (2H, m), 1.81-2.04 (2H, m), 2.70-2.74 (2H, m), 2.81 (1H, dd), 4.28 (2H, q), 5.38-5.47 (2H, m), 5.85-5.96 (1H, m)

PRODUCTION EXAMPLE 5

By using 0.25 g of α-bromo-γ-butyrolactone instead of tert-butyl bromoacetate according to Production Example 1 (2) was obtained 0.1 g of α-(1,1-dicyano-3-butenyl)-γ-butyrolactone (hereinafter referred to as the present invention compound (5)).

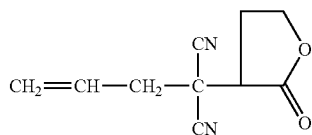

$^1$H-NMR (CDCl$_3$, TMS) δ (ppm): 2.41-2.73 (2H, m), 2.98-3.20 (3H, m), 4.26-4.35 (1H, m), 4.52-4.58 (1H, m), 5.48-5.53 (2H, m), 5.86-6.00 (1H, m)

PRODUCTION EXAMPLE 6

By using 0.27 g of α-bromo-γ-valerolactone instead of tert-butyl bromoacetate according to Production Example 1 (2) was obtained 0.12 g of α-(1,1-dicyano-3-butenyl)-γ-valerolactone (hereinafter referred to as the present invention compound (6)).

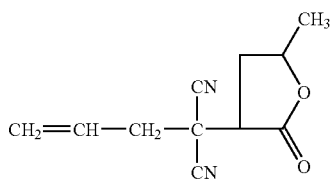

$^1$H-NMR (CDCl$_3$, TMS) δ (ppm): 1.55 (3H, dd), 1.98-2.10 (1H, m), 2.70-2.78 (1H, m), 2.98-3.26 (3H, m), 4.58-4.65 (1H, m), 5.47-5.52 (2H, m), 5.85-5.99 (1H, m)

PRODUCTION EXAMPLE 7

(1) 32 ml of N,N-dimethylformamide and 5.2 g of 2-(3,3,3-trifluoropropyl)malononitrile were mixed (hereinafter, thus obtained solution is referred to as solution B).

(2) 2 ml of solution B, 0.4 g of potassium carbonate and 0.36 g of ethyl 2-bromopropionate were mixed, and stirred for 4 hours at room temperature. Then, to the reaction mixture was added dilute hydrochloric acid, and extracted with ethyl acetate. The organic layer was washed successively with water and saturated brine, dried over anhydrous magnesium sulfate and concentrated under reduced pressure. The residue obtained was subjected to silica gel column chromatography to give 0.25 g of 2-[1-(ethoxycarbonyl)ethyl]-2-(3,3,3-trifluoropropyl)malononitrile (hereinafter referred to as the present invention compound (7)).

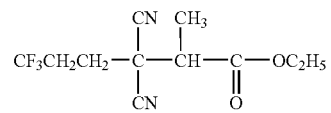

$^1$H-NMR (CDCl$_3$, TMS) δ (ppm): 1.33 (3H, t), 1.60 (3H, d), 2.21-2.35 (2H, m), 2.51-2.62 (2H, m), 2.98 (1H, q), 4.29 (2H, q)

PRODUCTION EXAMPLE 8

By using 0.39 g of ethyl 2-bromobutyrate instead of ethyl 2-bromopropionate according to Production Example 7 (2) was obtained 0.4 g of 2-[1-(ethoxycarbonyl)propyl]-2-(3,3,3-trifluoropropyl)malononitrile (hereinafter referred to as the present invention compound (8)).

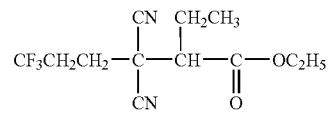

$^1$H-NMR (CDCl$_3$, TMS) δ (ppm): 1.10 (3H, t), 1.34 (3H, t), 1.95-2.13 (2H, m), 2.20-2.30 (2H, m), 2.48-2.65 (2H, m), 2.75 (1H, dd), 4.33 (2H, q)

PRODUCTION EXAMPLE 9

By using 0.42 g of ethyl 2-bromovalerate instead of ethyl 2-bromopropionate according to Production Example 7 (2) was obtained 0.35 g of 2-[1-(ethoxycarbonyl)butyl]-2-(3,3,3-trifluoropropyl)malononitrile (hereinafter referred to as the present invention compound (9)).

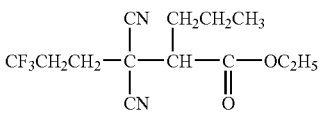

¹H-NMR (CDCl₃, TMS) δ (ppm): 0.90-1.05 (3H, m), 1.25-1.35 (3H, m), 1.30-1.55 (2H, m), 1.80-1.90 (1H, m), 1.95-2.10 (1H, m), 2.20-2.33 (2H, m), 2.48-2.65 (2H, m), 2.83 (1H, dd), 4.20-4.35 (2H, m)

PRODUCTION EXAMPLE 10

By using 0.45 g of ethyl 2-bromohexanoate instead of ethyl 2-bromopropionate according to Production Example 7 (2) was obtained 0.51 g of 2-[1-(ethoxycarbonyl)pentyl]-2-(3,3,3-trifluoropropyl)malononitrile (hereinafter referred to as the present invention compound (10)).

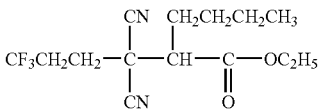

¹H-NMR (CDCl₃, TMS) δ (ppm): 0.94 (3H, m), 1.25-1.55 (7H, m), 1.80-2.15 (2H, m), 2.20-2.33 (2H, m), 2.48-2.65 (2H, m), 2.81 (1H, dd), 4.20-4.33 (2H, m)

PRODUCTION EXAMPLE 11

By using 0.45 g of ethyl chloroacetate instead of ethyl 2-bromopropionate according to Production Example 7 (2) was obtained 0.33 g of 2-(ethoxycarbonylmethyl)-2-(3,3,3-trifluoropropyl)malononitrile (hereinafter referred to as the present invention compound (11)).

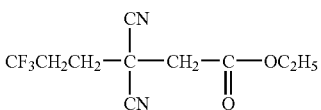

¹H-NMR (CDCl₃, TMS) δ (ppm): 1.34 (3H, t), 2.32-2.36 (2H, m), 2.51-2.62 (2H, m), 3.04 (2H, s), 4.31 (2H, q)

PRODUCTION EXAMPLE 12

(1) The mixture of 2.76 g of 2-(tert-butoxycarbonylmethyl)-2-(3,3,3-trifluoropropyl)malononitrile and 20 ml of trifluoracetic acid were stirred for 15 minutes at room temperature, and concentrated under reduced pressure. To the residue was added toluene, and concentrated again under reduced pressure. The obtained residue was dissolved in 10 ml of ethyl acetate. (Hereinafter, thus obtained solution is referred to as solution C).

(2) 1 ml of solution C, 0.2 ml of methanol, 0.46 g of triphenylphosphine, 2 ml of ethyl acetate and 0.5 ml of diisopropyl azodicarboxylate (40% toluene solution) were mixed and stirred for 15 minutes at room temperature. Then, to the reaction mixture was added 10 ml of hexane and the solution was filtered. The filtrate was subjected to silica gel column chromatography to give 0.17 g of 2-(methoxycarbonylmethyl)-2-(3,3,3-trifluoropropyl)malononitrile (hereinafter referred to as the present invention compound (12)).

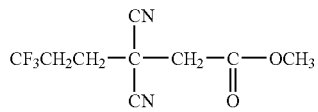

¹H-NMR (CDCl₃, TMS) δ (ppm): 2.32-2.36 (2H, m), 2.51-2.62 (2H, m), 3.06 (2H, s), 3.85 (3H, s)

PRODUCTION EXAMPLE 13

1 ml of solution B, 0.27 g of potassium carbonate and 0.15 g of butyl chloroacetate were mixed, and stirred for 4 hours at room temperature. Then, to the reaction mixture was added dilute hydrochloric acid, and extracted with ethyl acetate. The organic layer was washed successively with water and saturated brine, dried over anhydrous magnesium sulfate and concentrated under reduced pressure. The residue obtained was subjected to silica gel column chromatography to give 0.18 g of 2-(butoxycarbonylmethyl)-2-(3,3,3-trifluoropropyl)malononitrile (hereinafter referred to as the present invention compound (13)).

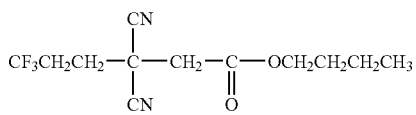

¹H-NMR (CDCl₃, TMS) δ (ppm): 0.94 (3H, m), 1.36-1.47 (2H, m), 1.62-1.71 (2H, m), 2.32-2.36 (2H, m), 2.50-2.61 (2H, m), 3.07 (2H, s), 4.24 (2H, t)

PRODUCTION EXAMPLE 14

By using 0.2 ml of isopropanol instead of methanol according to Production Example 12 (2) was obtained 0.16 g of 2-(isopropoxycarbonylmethyl)-2-(3,3,3-trifluoropropyl)malononitrile (hereinafter referred to as the present invention compound (14)).

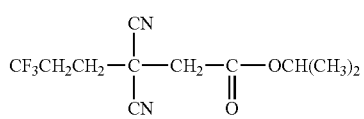

¹H-NMR (CDCl₃, TMS) δ (ppm): 1.32 (6H, d), 2.31-2.35 (2H, m), 2.51-2.62 (2H, m), 3.00 (2H, s), 5.16 (1H, m)

PRODUCTION EXAMPLE 15

By using 0.2 ml of isobutanol instead of methanol according to Production Example 12 (2) was obtained 0.14 g of 2-(isobutoxycarbonylmethyl)-2-(3,3,3-trifluoropropyl)malononitrile (hereinafter referred to as the present invention compound (15)).

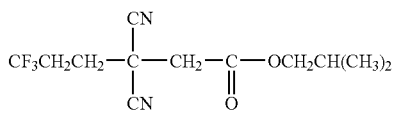

$^1$H-NMR (CDCl$_3$, TMS) δ (ppm): 0.97 (6H, d), 1.95-2.05 (1H, m), 2.32-2.36 (2H, m), 2.51-2.62 (2H, m), 3.06 (2H, s), 4.03 (2H, d)

PRODUCTION EXAMPLE 16

By using 0.2 ml of sec-butyl alcohol instead of methanol according to Production Example 12 (2) was obtained 0.12 g of 2-(sec-butoxycarbonylmethyl)-2-(3,3,3trifluoropropyl)malononitrile (hereinafter referred to as the present invention compound (16)).

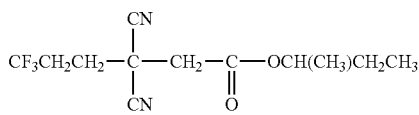

$^1$H-NMR (CDCl$_3$, TMS) δ (ppm): 0.94 (3H, t), 1.31 (3H, d), 1.55-1.72 (2H, m), 2.31-2.35 (2H, m), 2.50-2.62 (2H, m), 3.02 (2H, s), 4.99-5.03 (1H, m)

PRODUCTION EXAMPLE 17

By using 0.2 ml of allyl alcohol instead of methanol according to Production Example 12 (2) was obtained 0.18 g of 2-(allyloxycarbonylmethyl)-2-(3,3,3-trifluoropropyl)malononitrile (hereinafter referred to as the present invention compound (17)).

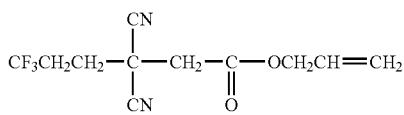

$^1$H-NMR (CDCl$_3$, TMS) δ (ppm): 2.32-2.36 (2H, m), 2.53-2.60 (2H, m), 3.08 (2H, s), 4.72-4.74 (2H, m), 5.32-5.42 (2H, m), 5.88-5.98 (1H, m)

PRODUCTION EXAMPLE 18

By using 0.2 ml of 2-butyne-1-ol instead of methanol according to Production Example 12 (2) was obtained 0.17 g of 2-[(2-butynyl)oxycarbonylmethyl]-2-(3,3,3-trifluoropropyl)malononitrile (hereinafter referred to as the present invention compound (18)).

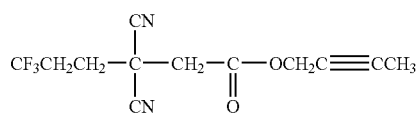

$^1$H-NMR (CDCl$_3$, TMS) δ (ppm): 1.87 (3H, t), 2.33-2.37 (2H, m), 2.51-2.62 (2H, m), 3.09 (2H, s), 4.80 (2H, q)

PRODUCTION EXAMPLE 19

By using 0.2 ml of 1-hexanol instead of methanol according to Production Example 12 (2) was obtained 0.18 g of 2-(hexyloxycarbonylmethyl)-2-(3,3,3-trifluoropropyl)malononitrile (hereinafter referred to as the present invention compound (19)).

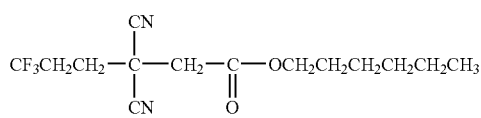

$^1$H-NMR (CDCl$_3$, TMS) δ (ppm): 0.90 (3H, m), 1.29-1.41 (6H, m), 1.62-1.72 (2H, m), 2.32-2.36 (2H, m), 2.51-2.62 (2H, m), 3.04 (2H, s), 4.24 (2H, t)

PRODUCTION EXAMPLE 20

By using 0.2 ml of cyclohexanol instead of methanol according to Production Example 12 (2) was obtained 0.09 g of 2-(cyclohexyloxycarbonylmethyl)-2-(3,3,3-trifluoropropyl)malononitrile (hereinafter referred to as the present invention compound (20)).

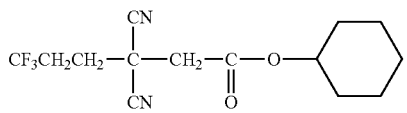

$^1$H-NMR (CDCl$_3$, TMS) δ (ppm): 1.26-1.57 (6H, m), 1.74-1.77 (2H, m), 1.87-1.92 (2H, m), 2.32-2.35 (2H, m), 2.53-2.59 (2H, m), 3.02 (2H, s), 4.92-4.96 (1H, m)

PRODUCTION EXAMPLE 21

(1) 21 ml of N,N-dimethylformamide and 4.32 g of 2-(tert-butoxycarbonylmethyl)malononitrile were mixed (hereinafter, thus obtained solution is referred to as solution D).

(2) 1 ml of solution D, 0.27 g of potassium carbonate and 0.14 g of 3-bromopropionitrile were mixed, and stirred for 4 hours at room temperature. Then, to the reaction mixture was added dilute hydrochloric acid, and extracted with ethyl acetate. The organic layer was washed successively with water and saturated brine, dried over anhydrous magnesium sulfate and concentrated under reduced pressure. The residue obtained was subjected to silica gel column chromatography to give 0.15 g of 2-(tert-butoxycarbonylmethyl)-2-(2-cyanoethyl)malononitrile (hereinafter referred to as the present invention compound (21)).

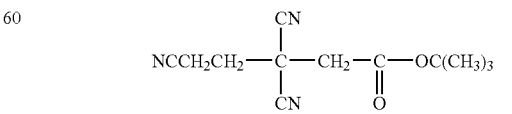

$^1$H-NMR (CDCl$_3$, TMS) δ (ppm): 1.53 (9H, s), 2.45-2.49 (2H, m), 2.78-2.82 (2H, m), 2.96 (2H, s)

PRODUCTION EXAMPLE 22

By using 0.15 g of 4-bromobutyronitrile instead of 3-bromopropionitrile according to Production Example 21 (2) was obtained 0.24 g of 2-(tert-butoxycarbonylmethyl)-2-(3-cyanopropyl)malononitrile (hereinafter referred to as the present invention compound (22)).

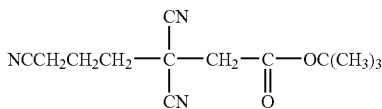

$^1$H-NMR (CDCl$_3$, TMS) δ (ppm): 1.53 (9H, s), 2.06-2.16 (2H, m), 2.17-2.22 (2H, m), 2.54-2.60 (2H, m), 2.92 (2H, s)

PRODUCTION EXAMPLE 23

By using 0.13 g of 1-bromo-2-fluoroethane instead of 3-bromopropionitrile according to Production Example 21 (2) was obtained 0.12 g of 2-(tert-butoxycarbonylmethyl)-2-(2-fluoroethyl)malononitrile (hereinafter referred to as the present invention compound (23)).

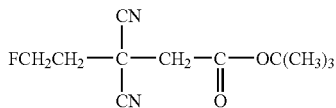

$^1$H-NMR (CDCl$_3$, TMS) δ (ppm): 1.52 (9H, s), 2.49 (1H, t), 2.56 (1H, t), 2.99 (2H, s), 4.74 (1H, t), 4.86 (1H, t)

PRODUCTION EXAMPLE 24

By using 0.16 g of 1-bromo-3-chloropropane instead of 3-bromopropionitrile according to Production Example 21 (2) was obtained 0.17 g of 2-(tert-butoxycarbonylmethyl)-2-(3-chloropropyl)malononitrile (hereinafter referred to as the present invention compound (24)).

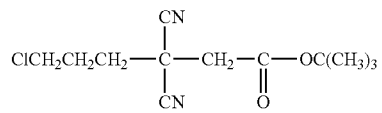

$^1$H-NMR (CDCl$_3$, TMS) δ (ppm): 1.52 (9H, s), 2.18-2.27 (4H, m), 2.91 (2H, s), 3.63-3.69 (2H, m)

PRODUCTION EXAMPLE 25

By using 0.18 g of 1-bromo-3-chloro-2-methylpropane instead of 3-bromopropionitrile according to Production Example 21 (2) was obtained 0.21 g of 2-(tert-butoxycarbonylmethyl)-2-(3-chloro-2-methylpropyl)malononitrile (hereinafter referred to as the present invention compound (25)).

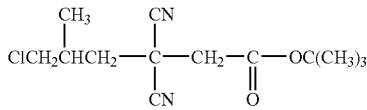

$^1$H-NMR (CDCl$_3$, TMS) δ (ppm): 1.29 (3H, d), 1.53 (9H, s), 1.91-1.96 (1H, m), 2.29-2.42 (2H, m), 2.92 (2H, s), 3.49-3.55 (1H, m), 3.66-3.70 (1H, m)

PRODUCTION EXAMPLE 26

By using 0.18 g of 1-bromo-4-chlorobutane instead of 3-bromopropionitrile according to Production Example 21 (2) was obtained 0.19 g of 2-(tert-butoxycarbonylmethyl)-2-(4-chlorobutyl)malononitrile (hereinafter referred to as the present invention compound (26)).

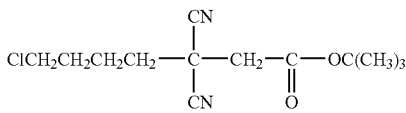

$^1$H-NMR (CDCl$_3$, TMS) δ (ppm): 1.53 (9H, s), 1.87-1.92 (4H, m), 2.04-2.08 (2H, m), 2.89 (2H, s), 3.59 (2H, t)

PRODUCTION EXAMPLE 27

By using 0.15 g of 1-bromo-3-methyl-2-butene instead of 3-bromopropionitrile according to Production Example 21 (2) was obtained 0.13 g of 2-(tert-butoxycarbonylmethyl)-2-(3-methyl-2-butenyl)malononitrile (hereinafter referred to as the present invention compound (27)).

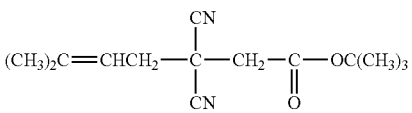

$^1$H-NMR (CDCl$_3$, TMS) δ (ppm): 1.53 (9H, s), 1.76 (3H, s), 1.82 (3H, s), 2.11-2.34 (1H, m), 2.77 (2H, d), 2.85 (2H, s)

PRODUCTION EXAMPLE 28

By using 0.15 g of 1-bromobutane instead of 3bromopropionitrile according to Production Example 21 (2) was obtained 0.15 g of 2-(tert-butoxycarbonylmethyl)-2-butylmalononitrile (hereinafter referred to as the present invention compound (28)).

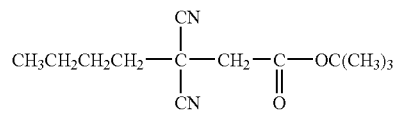

$^1$H-NMR (CDCl$_3$, TMS) δ (ppm): 0.98 (3H, t), 1.40-1.50 (2H, m), 1.53 (9H, s), 1.55-1.76 (2H, m), 1.98-2.02 (2H, m), 2.87 (2H, s)

PRODUCTION EXAMPLE 29

By using 0.15 g of 1-bromopentane instead of 3-bromopropionitrile according to Production Example 21 (2) was obtained 0.19 g of 2-(tert-butoxycarbonylmethyl)-2-pentylmalononitrile (hereinafter referred to as the present invention compound (29)).

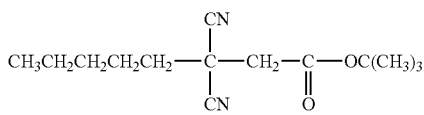

$^1$H-NMR (CDCl$_3$, TMS) δ (ppm): 0.90-0.96 (3H, m), 1.35-1.43 (4H, m), 1.53 (9H, s), 1.66-1.73 (2H, m), 1.97-2.01 (2H, m), 2.86 (2H, s)

PRODUCTION EXAMPLE 30

By using 0.17 g of 1-bromohexane instead of 3-bromopropionitrile according to Production Example 21 (2) was obtained 0.26 g of 2-(tert-butoxycarbonylmethyl)-2-hexylmalononitrile (hereinafter referred to as the present invention compound (30)).

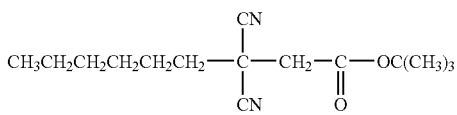

$^1$H-NMR (CDCl$_3$, TMS) δ (ppm): 0.88-0.92 (3H, m), 1.31-1.44 (6H, m), 1.53 (9H, s), 1.65-1.73 (2H, m), 1.97-2.01 (2H, m), 2.86 (2H, s)

PRODUCTION EXAMPLE 31

By using 0.15 g of 1-bromo-3-methylbutane instead of 3-bromopropionitrile according to Production Example 21 (2) was obtained 0.16 g of 2-(tert-butoxycarbonylmethyl)-2-(3-methylbutyl)malononitrile (hereinafter referred to as the present invention compound (31)).

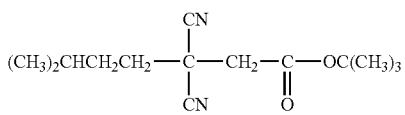

$^1$H-NMR (CDCl$_3$, TMS) δ (ppm): 0.96 (6H, d), 1.53 (9H, s), 1.50-1.71 (3H, m), 1.98-2.02 (2H, m), 2.86 (2H, s)

PRODUCTION EXAMPLE 32

By using 0.16 g of 2-bromobutane instead of 3-bromopropionitrile according to Production Example 21 (2) was obtained 0.13 g of 2-(tert-butoxycarbonylmethyl)-2-(1-methylpropyl)malononitrile (hereinafter referred to as the present invention compound (32)).

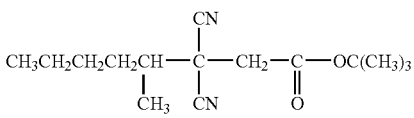

$^1$H-NMR (CDCl$_3$, TMS) δ (ppm): 1.04 (3H, t), 1.22 (3H, d), 1.33-1.45 (1H, m), 1.53 (9H, s), 1.83-1.92 (1H, m), 1.97-2.06 (1H, m), 2.86 (2H, dd)

PRODUCTION EXAMPLE 33

By using 0.17 g of 2-bromohexane instead of 3-bromopropionitrile according to Production Example 21 (2) was obtained 0.11 g of 2-(tert-butoxycarbonylmethyl)-2-(1-methylpentyl)malononitrile (hereinafter referred to as the present invention compound (33)).

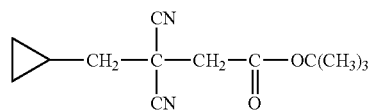

$^1$H-NMR (CDCl$_3$, TMS) δ (ppm): 0.93 (3H, t), 1.21 (3H, d), 1.27-1.59 (5H, m), 1.53 (9H, s), 1.70-1.80 (1H, m), 2.03-2.15 (1H, m), 2.86 (2H, dd)

PRODUCTION EXAMPLE 34

By using 0.15 g of (bromomethyl)cyclopropane instead of 3-bromopropionitrile according to Production Example 21 (2) was obtained 0.2 g of 2-(tert-butoxycarbonylmethyl)-2-(cyclopropylmethyl)malononitrile (hereinafter referred to as the present invention compound (34)).

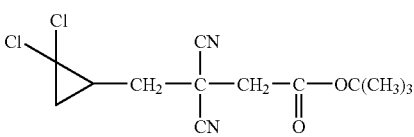

$^1$H-NMR (CDCl$_3$, TMS) δ (ppm): 0.37-0.43 (2H, m), 0.69-0.77 (2H, m), 1.00-1.10 (1H, m), 1.53 (9H, s), 2.02 (2H, d), 2.93 (2H, s)

PRODUCTION EXAMPLE 35

By using 0.2 g of 2,2-dichloro-1-(bromomethyl)cyclopropane instead of 3-bromopropionitrile according to Production Example 21 (2) was obtained 0.22 g of 2-(tert-butoxycarbonylmethyl)-2-[(2,2-dichlorocyclopropyl)methyl]malononitrile (hereinafter referred to as the present invention compound (35)).

$^1$H-NMR (CDCl$_3$, TMS) δ (ppm): 1.42-1.50 (1H, m), 1.53 (9H, s), 1.87-1.96 (2H, m), 2.11-2.21 (1H, m), 2.53-2.58 (1H, m), 2.96 (2H, dd)

PRODUCTION EXAMPLE 36

By using 0.15 g of 1-bromo-2-butene instead of 3-bromopropionitrile according to Production Example 21 (2) was obtained 0.16 g of 2-(tert-butoxycarbonylmethyl)-2-(2-butenyl)malononitrile (hereinafter referred to as the present invention compound (36)).

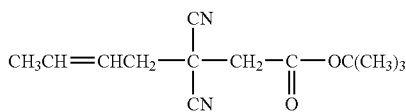

$^1$H-NMR (CDCl$_3$, TMS) δ (ppm): 1.52 (9H, s), 1.79 (3H, d), 2.71 (2H, d), 2.84 (2H, s), 5.34-5.56 (1H, m), 5.70-6.00 (1H, m)

PRODUCTION EXAMPLE 37

2 ml of solution D, 0.42 g of potassium carbonate and 0.15 g of 1-bromopropane were mixed, and stirred for 4 hours at room temperature. Then, to the reaction mixture was added dilute hydrochloric acid, and extracted with ethyl acetate. The organic layer was washed successively with water and saturated brine, dried over anhydrous magnesium sulfate and concentrated under reduced pressure. The residue obtained was subjected to silica gel column chromatography to give 0.14 g of 2-(tert-butoxycarbonylmethyl)-2-propylmalononitrile (hereinafter referred to as the present invention compound (37)).

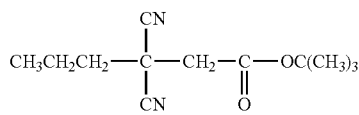

$^1$H-NMR (CDCl$_3$, TMS) δ (ppm): 1.06 (3H, t), 1.53 (9H, s), 1.68-1.82 (2H, m), 1.96-2.05 (2H, m), 2.87 (2H, s)

PRODUCTION EXAMPLE 38

(1) 24 ml of N,N-dimethylformamide and 2.93 g of 2butylmalononitrile were mixed (hereinafter, thus obtained solution is referred to as solution E).

(2) 1 ml of solution E, 0.27 g of potassium carbonate and 0.18 g of ethyl 2-bromopropionate were mixed, and stirred for 4 hours at room temperature. Then, to the reaction mixture was added dilute hydrochloric acid, and extracted with ethyl acetate. The organic layer was washed successively with water and saturated brine, dried over anhydrous magnesium sulfate and concentrated under reduced pressure. The residue obtained was subjected to silica gel column chromatography to give 0.15 g of 2-[1-(ethoxycarbonyl)ethyl]-2-butylmalononitrile (hereinafter referred to as the present invention compound (38)).

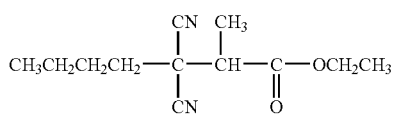

$^1$H-NMR (CDCl$_3$, TMS) δ (ppm): 0.98 (3H, t), 1.31 (3H, t), 1.42 (2H, q), 1.55 (3H, d), 1.60-1.80 (2H, m), 1.95-2.00 (2H, m), 2.93 (1H, q), 4.27 (2H, q)

PRODUCTION EXAMPLE 39

By using 0.21 g of tert-butyl 2-bromopropionate instead of ethyl 2-bromopropionate according to Production Example 38 (2) was obtained 0.14 g of 2-[1-(tert-butoxycarbonyl)ethyl]-2-butylmalononitrile (hereinafter referred to as the present invention compound (39)).

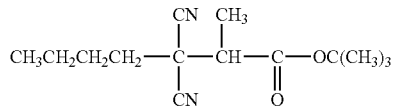

$^1$H-NMR (CDCl$_3$, TMS) δ (ppm): 0.98 (3H, t), 1.35-1.50 (2H, m), 1.48 (3H, d), 1.50 (9H, s), 1.63-1.73 (2H, m), 1.92-2.02 (2H, m), 2.81 (1H, q)

PRODUCTION EXAMPLE 40

By using 0.19 g of 1-bromo-3,4,4-trifluoro-3-butene instead of 1-bromopropane according to Production Example 37 was obtained 0.13 g of 2-(tert-butoxycarbonylmethyl)-2-(3,4,4-trifluoro-3-butenyl)malononitrile (hereinafter referred to as the present invention compound (40)).

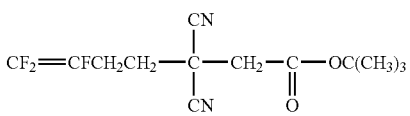

$^1$H-NMR (CDCl$_3$, TMS) δ (ppm): 1.53 (9H, s), 2.27-2.31 (2H, m), 2.68-2.79 (2H, m), 2.93 (2H, s)

PRODUCTION EXAMPLE 41

By using 0.2 g of ethyl 2-bromobutyrate instead of ethyl 2-bromopropionate according to Production Example 38 (2) was obtained 0.19 g of 2-[1-(ethoxycarbonyl)propyl]-2-butylmalononitrile (hereinafter referred to as the present invention compound (41)).

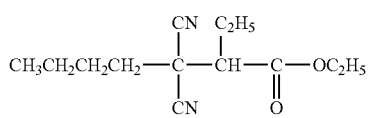

$^1$H-NMR (CDCl$_3$, TMS) δ (ppm): 0.97 (3H, t), 1.05 (3H, t), 1.35 (3H, t), 1.43 (2H, q), 1.65-1.73 (2H, m), 1.88-2.04 (4H, m), 2.71 (1H, dd), 4.28 (2H, q)

PRODUCTION EXAMPLE 42

By using 0.17 g of α-bromo-γ-butyrolactone instead of ethyl 2-bromopropionate according to Production Example 38 (2) was obtained 0.1 g of α-(1,1-dicyanohexyl)-γ-butyrolactone (hereinafter referred to as the present invention compound (42)).

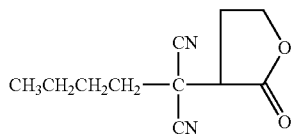

¹H-NMR (CDCl₃, TMS) δ (ppm): 0.99 (3H, t), 1.48 (2H, q), 1.67-1.75 (2H, m), 2.02-2.09 (1H, m), 2.40-2.50 (2H, m), 2.65-2.69 (1H, m), 3.12-3.17 (1H, dd), 4.27-4.34 (1H, m), 4.52-4.57 (1H, m)

PRODUCTION EXAMPLE 43

By using 0.18 g of α-bromo-γ-valerolactone instead of ethyl 2-bromopropionate according to Production Example 38 (2) was obtained 0.15 g of α-(1,1-dicyanohexyl)-γ-valerolactone (hereinafter referred to as the present invention compound (43)).

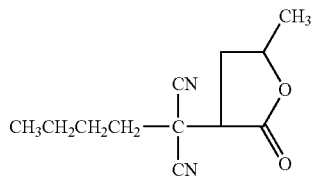

¹H-NMR (CDCl₃, TMS) δ (ppm): 0.99 (3H, t), 1.48 (2H, q), 1.53 (3H, d), 1.66-1.73 (2H, m), 1.96-2.08 (2H, m), 2.41-2.50 (1H, m), 2.71-2.77 (1H, m), 3.19-3.24 (1H, dd), 4.59-4.64 (1H, m)

PRODUCTION EXAMPLE 44

By using 0.2 g of tert-butyl bromoacetate instead of ethyl 2-bromopropionate according to Production Example 7 (2) was obtained 0.18 g of 2-(tert-butoxycarbonylmethyl)-2-(3,3,3-trifluoropropyl)malononitrile (hereinafter referred to as the present invention compound (44)).

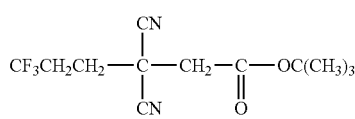

¹H-NMR (CDCl₃, TMS) δ (ppm): 1.53 (9H, s), 2.28-2.32 (2H, m), 2.49-2.61 (2H, m), 2.94 (2H, s)

PRODUCTION EXAMPLE 45

By using 0.07 g of tert-butyl bromothio-O-acetate (BrCH₂C(=S)OC(CH₃)₃) instead of ethyl 2-bromopropionate according to Production Example 7 (2) was obtained 0.03 g of 2-[tert-butoxy(thiocarbonyl)methyl]-2-(3,3,3-trifluoropropyl)malononitrile (hereinafter referred to as the present invention compound (45)).

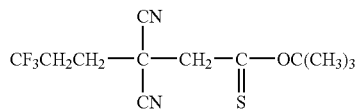

¹H-NMR (CDCl₃, TMS) δ (ppm): 1.53 (9H, s), 2.28-2.30 (2H, m), 2.49-2.60 (2H, m), 3.14 (2H, s)

PRODUCTION EXAMPLE 46

By using 0.21 g of tert-butyl 1-bromopropionate instead of ethyl 2-bromopropionate according to Production Example 7 (2) was obtained 0.12 g of 2-[1-(tert-butoxycarbonyl)ethyl]-2-(3,3,3-trifluoropropyl)malononitrile (hereinafter referred to as the present invention compound (46)).

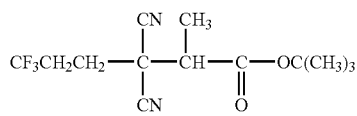

¹H-NMR (CDCl₃, TMS) δ (ppm): 1.51 (9H, s), 1.55 (3H, d), 2.22-2.28 (2H, m), 2.51-2.69 (2H, m), 2.85 (1H, q)

PRODUCTION EXAMPLE 47

2.8 g of 2-(3,3,3-trifluoropropyl)malononitrile and 3.5 g of tert-butyl bromothio-S-acetate (BrCH₂C(=O)SC(CH₃)₃) were dissolved in 15 ml of N,N-dimethylformamide, and to the solution was added 2.3 g of potassium carbonate followed by stirring for 5 hours at room temperature. Then, to the reaction mixture was added dilute hydrochloric acid, and extracted with ethyl acetate. The organic layer was washed successively with water and saturated brine, dried over anhydrous magnesium sulfate and concentrated under reduced pressure. The residue obtained was subjected to silica gel column chromatography to give 0.4 g of 2-[(tert-butylthio)carbonylmethyl]-2-(3,3,3-trifluoropropyl)malononitrile (hereinafter referred to as the present invention compound (47)).

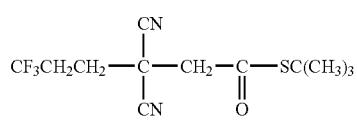

¹H-NMR (CDCl₃, TMS) δ (ppm): 1.52 (9H, S), 2.25-2.33 (2H, m), 2.48-2.61 (2H, m), 3.13 (2H, S)

PRODUCTION EXAMPLE 48

By using 0.13 g of methyl chloroacetate instead of ethyl 2-bromopropionate according to Production Example 38 (2) was obtained 0.15 g of 2-(methoxycarbonylmethyl)-2-butylmalononitrile (hereinafter referred to as the present invention compound (48)).

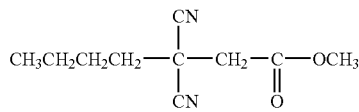

¹H-NMR (CDCl₃, TMS) δ (ppm): 0.93 (3H, t), 1.38-1.49 (2H, m), 1.68-1.74 (2H, m), 1.97-2.09 (2H, m), 2.97 (2H, s), 3.82 (3H, s)

PRODUCTION EXAMPLE 49

By using 0.14 g of ethyl chloroacetate instead of ethyl 2-bromopropionate according to Production Example 38 (2) was obtained 0.18 g of 2-(ethoxycarbonylmethyl)-2-butyl-malononitrile (hereinafter referred to as the present invention compound (49)).

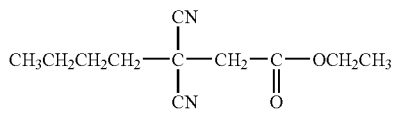

¹H-NMR (CDCl₃, TMS) δ (ppm): 0.98 (3H, t), 1.35 (3H, t), 1.47-1.86 (2H, m), 1.61-1.72 (2H, m), 1.98-2.07 (2H, m), 2.97 (2H, s), 4.32 (2H, q)

PRODUCTION EXAMPLE 50

By using 0.15 g of butyl chloroacetate instead of ethyl 2-bromopropionate according to Production Example 38 (2) was obtained 0.17 g of 2-(butoxycarbonylmethyl)-2-butyl-malononitrile (hereinafter referred to as the present invention compound (50)).

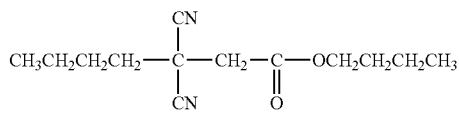

1H-NMR (CDCl₃, TMS) δ (ppm): 0.91-1.06 (6H, m), 2.38-2.50 (4H, m), 1.59-1.72 (4H, m), 2.01-2.08 (2H, m), 2.97 (2H, s), 4.23 (2H, s)

PRODUCTION EXAMPLE 51

0.48 g of 2-(tert-butoxycarbonylmethyl)malononitrile and 0.32 g of 1,1,1-trifluoro-4-bromobutane were dissolved in 2 ml of N,N-dimethylformamide, and to the solution was added 0.40 g of potassium carbonate followed by stirring for 5 hours at room temperature. Then, to the reaction mixture was added dilute hydrochloric acid, and extracted with ethyl acetate. The organic layer was washed successively with water and saturated brine, dried over anhydrous magnesium sulfate and concentrated under reduced pressure. The residue obtained was subjected to silica gel column chromatography to give 0.33 g of 2-(tert-butoxycarbonylmethyl)-2-(4,4,4-trifluorobutyl)malononitrile (hereinafter referred to as the present invention compound (51)).

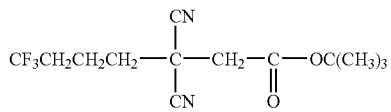

¹H-NMR (CDCl₃, TMS) δ (ppm): 1.53 (9H, s), 1.92-2.04 (2H, m), 2.07-2.12 (2H, m), 2.16-2.26 (2H, m), 2.88 (2H, s)

PRODUCTION EXAMPLE 52

By using 0.10 g of 2,2,2-trifluoroethanol instead of methanol according to Production Example 12 (2) was obtained 0.06 g of 2-[(2,2,2-trifluoroethoxy)carbonylmethyl]-2-(3,3,3-trifluoropropyl)malononitrile (hereinafter referred to as the present invention compound (52)).

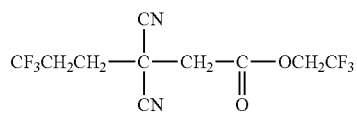

¹H-NMR (CDCl₃, TMS) δ (ppm): 2.31-2.36 (2H, m), 2.48-2.61 (2H, m), 3.18 (2H, m), 4.62 (2H, q)

PRODUCTION EXAMPLE 53

By using 0.09 g of 2,2-dimethylpropanol instead of methanol according to Production Example 12 (2) was obtained 0.03 g of 2-[(2,2-dimethylpropoxy)carbonylmethyl]-2-(3,3,3-trifluoropropyl)malononitrile (hereinafter referred to as the present invention compound (53)).

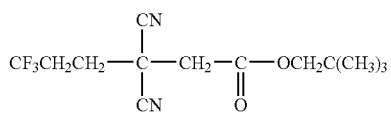

¹H-NMR (CDCl₃, TMS) δ (ppm): 0.97 (9H, s), 2.28-2.33 (2H, m), 2.49-2.62 (2H, m), 3.08 (2H, s), 3.90 (2H, s)

PRODUCTION EXAMPLE 54

By using 0.08 g of 2-chloroethanol instead of methanol according to Production Example 12 (2) was obtained 0.06 g of 2-[(2-chloroethoxy)carbonylmethyl]-2-(3,3,3-trifluoropropyl)malononitrile (hereinafter referred to as the present invention compound (54)).

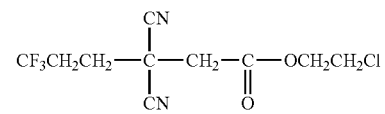

¹H-NMR (CDCl₃, TMS) δ (ppm): 2.28-2.33 (2H, m), 2.49-2.61 (2H, m), 3.09 (2H, s), 3.72 (2H, t), 4.49 (2H, t)

PRODUCTION EXAMPLE 55

By using 0.09 g of 1-chloro-2-propanol instead of methanol according to Production Example 12 (2) was obtained 0.03 g of 2-[(2-chloro-1-methylethoxy)carbonylmethyl]-2-(3,3,3-trifluoropropyl)malononitrile (hereinafter referred to as the present invention compound (55)).

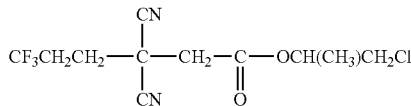

$^1$H-NMR (CDCl$_3$, TMS) δ (ppm): 1.39 (3H, d), 2.28-2.32 (2H, m)., 2.48-2.57 (2H, m), 3.06 (2H, s), 3.52-3.66 (2H, m), 5.18-5.26 (1H, m)

PRODUCTION EXAMPLE 56

By using 0.09 g of 3-chloropropanol instead of methanol according to Production Example 12 (2) was obtained 0.07 g of 2-[(3-chloropropoxy)carbonylmethyl]-2-(3,3,3-trifluoropropyl)malononitrile (hereinafter referred to as the present invention compound (56)).

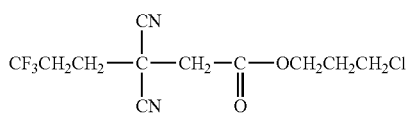

$^1$H-NMR (CDCl$_3$, TMS) δ (ppm): 2.16-2.21 (2H, m), 2.26-2.32 (2H, m), 2.48-2.60 (2H, m), 3.04 (2H, s), 3.62 (2H, t), 4.37 (2H, t)

PRODUCTION EXAMPLE 57

The mixture of 0.17 g of 2-methyl-3-butyne-2-ol, 0.3 ml of triethylamine, 0.12 g of 4-dimethylaminopyridine and 0.16 ml of chloroacetyl chloride was stirred for 5 minutes at room temperature and further for 2 hours at 60° C. The reaction mixture was cooled to room temperature, and 2 ml of solution B and 0.4 g of potassium carbonate were added thereto followed by stirring for 4 hours at room temperature. To the reaction mixture was added water and extracted with ethyl acetate. The organic layer was washed successively with water and saturated brine, dried over anhydrous magnesium sulfate and concentrated under reduced pressure. The residue obtained was subjected to silica gel column chromatography to give 0.02 g of 2-[(1,1-dimethyl-2-propynyl)oxycarbonylmethyl]-2-(3,3,3-trifluoropropyl)malononitrile (hereinafter referred to as the present invention compound (57)).

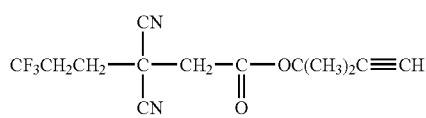

$^1$H-NMR (CDCl$_3$, TMS) δ (ppm): 1.52 (6H, s), 2.57-2.81 (2H, m), 2.48-2.58 (2H, m), 2.61 (1H, s), 2.98 (2H, s)

PRODUCTION EXAMPLE 58

By using 0.20 g of 3-methyl-1-pentyne-3-ol instead of 2-methyl-3-butyne-2-ol according to Production Example 57 was obtained 0.01 g of 2-((1-ethyl-1-methyl-2-propynyloxycarbonyl)methyl)-2-(3,3,3-trifluoropropyl)malononitrile (hereinafter referred to as the present invention compound (58)).

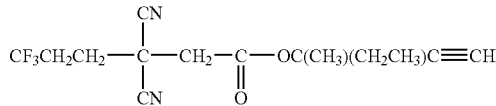

$^1$H-NMR (CDCl$_3$, TMS) δ (ppm): 1.02 (3H, t), 1.73 (3H, s), 1.87-2.18 (2H, m), 2.26-2.31 (2H, m), 2.47-2.55 (2H, m), 2.60 (1H, s), 3.01 (2H, s)

PRODUCTION EXAMPLE 59

By using 0.24 g of 3-methyl-3-methoxybutanol instead of 2-methyl-3-butyne-2-ol according to Production Example 57 was obtained 0.11 g of 2-[(3-methyl-3-methoxybutoxy)carbonylmethyl]-2-(3,3,3-trifluoropropyl)malononitrile (hereinafter referred to as the present invention compound (59)).

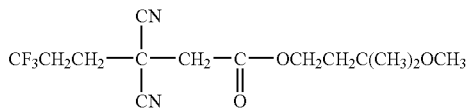

$^1$H-NMR (CDCl$_3$, TMS) δ (ppm): 1.18 (6H, s), 1.84 (2H, t), 2.27-2.31 (2H, m), 2.47-2.58 (2H, m), 3.02 (3H, s), 3.17 (3H, s), 4.31 (2H, t)

PRODUCTION EXAMPLE 60

By using 0.17 g of 1,1-dimethyl-2-propenyl alcohol instead of 2-methyl-3-butyne-2-ol according to Production Example 57 was obtained 0.01 g of 2-[(1,1-dimethyl-2-propenyl)oxycarbonylmethyl]-2-(3,3,3-trifluoropropyl)malononitrile (hereinafter referred to as the present invention compound (60)).

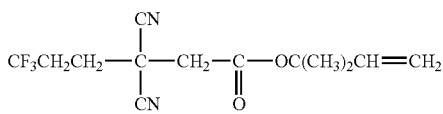

$^1$H-NMR (CDCl$_3$, TMS) δ (ppm): 1.60 (6H, s), 2.30-2.38 (2H, m), 2.47-2.57 (2H, m), 2.95 (2H, s), 5.27 (2H, dd), 6.08 (1H, dd)

PRODUCTION EXAMPLE 61

By using 0.20 g of 1,3-dimethylbutanol instead of 2-methyl-3-butyne-2-ol according to Production Example 57 was obtained 0.11 g of 2-[(1,3-dimethylbutoxy)carbonylmethyl]-2-(3,3,3-trifluoropropyl)malononitrile (hereinafter referred to as the present invention compound (61)).

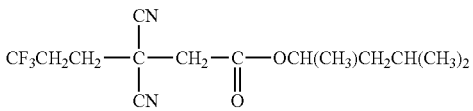

$^1$H-NMR (CDCl$_3$, TMS) δ (ppm): 0.98 (6H, d), 1.26 (3H, d), 1.58-1.65 (2H, m), 2.23-2.31 (2H, m), 2.44-2.56 (2H, m), 2.97 (2H, s), 5.13 (1H, m)

PRODUCTION EXAMPLE 62

By using 0.18 g of 1,2-dimethylpropanol instead of 2-methyl-3-butyne-2-ol according to Production Example 57 was obtained 0.10 g of 2-[(1,2-dimethylpropoxy)carbonylmethyl]-2-(3,3,3-trifluoropropyl)malononitrile (hereinafter referred to as the present invention compound (62)).

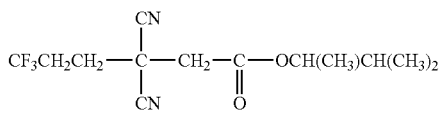

$^1$H-NMR (CDCl$_3$, TMS) δ (ppm): 0.93 (6H, d), 1.21 (3H, d), 1.81-1.89 (1H, m), 2.23-2.31 (2H, m), 2.47-2.58 (2H, m), 3.02 (2H, s), 4.88 (1H, m)

PRODUCTION EXAMPLE 63

2 ml of solution B, 0.42 g of potassium carbonate and 0.20 g of (1-cyano-1-methylethyl) chloroacetate were mixed and stirred for 4 hours at room temperature and further for 3 hours at 50° C. To the reaction mixture was added water and extracted with ethyl acetate. The organic layer was washed successively with water and saturated brine, dried over anhydrous magnesium sulfate and concentrated under reduced pressure. The residue obtained was subjected to silica gel column chromatography to give 0.03 g of 2-[(1-cyano-1-methylethoxy)carbonylmethyl]-2-(3,3,3-trifluoropropyl)malononitrile (hereinafter referred to as the present invention compound (63)).

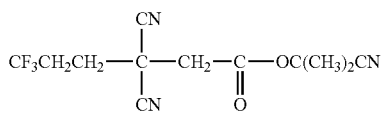

$^1$H-NMR (CDCl$_3$, TMS) δ (ppm): 1.82 (6H, s), 2.32-2.38 (2H, m), 2.52-2.61 (2H, m), 3.09 (2H, s)

PRODUCTION EXAMPLE 64

By using 0.17 g of (1,1-dimethyl-2-propynyl) 2-chloropropionate instead of (1-cyano-1-methylethyl) chloroacetate according to Production Example 63 was obtained 0.11 g of 2-(1-[(1,1-dimethyl-2-propynyl)oxycarbonyl]ethyl)-2-(3,3,3-trifluoropropyl)malononitrile (hereinafter referred to as the present invention compound (64)).

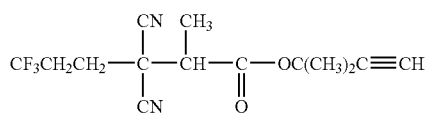

$^1$H-NMR (CDCl$_3$, TMS) δ (ppm): 1.56 (2H, d), 1.68 (6H, s), 2.21-2.29 (2H, m), 2.48-2.59 (2H, m), 2.60 (1H, s), 2.91 (1H, q)

PRODUCTION EXAMPLE 65

By using 0.19 g of (1-ethyl-1-methyl-2-propynyl) 2-chloropropionate instead of (1-cyano-1-methylethyl) chloroacetate according to Production Example 63 was obtained 0.09 g of 2-(1-[(1-ethyl-1-methyl-2-propynyl)oxycarbonyl]ethyl)-2-(3,3,3-trifluoropropyl)malononitrile (hereinafter referred to as the present invention compound (65)).

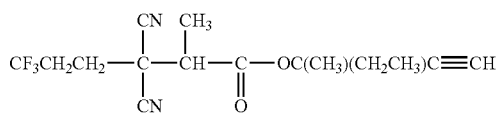

$^1$H-NMR (CDCl$_3$, TMS) δ (ppm): 1.03 (3H, t), 1.56 (3H, d), 1.68 (3H, s), 1.88-2.03 (2H, m), 2.18-2.27 (2H, m), 2.46-2.54 (2H, m), 2.55 (1H, s), 2.89 (1H, q)

PRODUCTION EXAMPLE 66

By using 0.18 g of (1-cyano-1-methylethyl) 2-chloropropionate instead of (1-cyano-1-methylethyl) chloroacetate according to Production Example 63 was obtained 0.07 g of 2-(1-[(1-cyano-1-methylethoxy)carbonyl]ethyl)-2-(3,3,3-trifluoropropyl)malononitrile (hereinafter referred to as the present invention compound (66)).

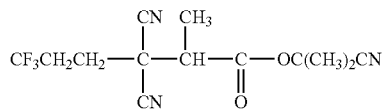

$^1$H-NMR (CDCl$_3$, TMS) δ (ppm): 1.58 (3H, d), 1.78 (6H, s), 2.21-2.26 (2H, m), 2.48-2.59 (2H, m), 3.01 (1H, q)

PRODUCTION EXAMPLE 67

By using 0.18 g of (1,1-dimethyl-2-propenyl) 2-chloropropionate instead of (1-cyano-1-methylethyl) chloroacetate according to Production Example 63 was obtained 0.12 g of 2-(1-[(1,1-dimethyl-2-propenyl)oxycarbonyl]ethyl)-2-(3,3,3-trifluoropropyl)malononitrile (hereinafter referred to as the present invention compound (67)).

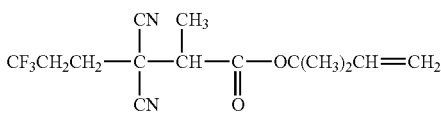

$^1$H-NMR (CDCl$_3$, TMS) δ (ppm): 1.54 (3H, d), 1.58 (6H, s), 2.18-2.24 (2H, m), 2.42-2.51 (2H, m), 2.85 (1H, q), 5.19 (2H, dd), 6.06 (1H, dd)

PRODUCTION EXAMPLE 68

By using 0.21 g of (3-methyl-3-methoxybutyl) 2-chloropropionate instead of (1-cyano-1-methylethyl) chloroacetate according to Production Example 63 was obtained 0.13 g of 2-(1-[(3-methyl-3-methoxybutoxy)carbonyl]ethyl)-2-(3,3,3-trifluoropropyl)malononitrile (hereinafter referred to as the present invention compound (68)).

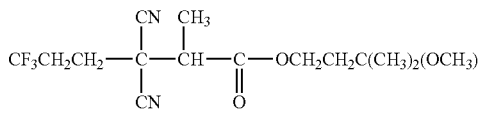

$^1$H-NMR (CDCl$_3$, TMS) δ (ppm): 1.20 (6H, s), 1.57 (3H, d), 1.83 (2H, t), 2.07-2.29 (2H, m), 2.48-2.56 (2H, m), 2.92 (1H, q), 3.13 (3H, s), 4.32 (2H, t)

PRODUCTION EXAMPLE 69

By using 0.19 g of (1,3-dimethylbutyl) 2-chloropropionate instead of (1-cyano-1-methylethyl) chloroacetate according to Production Example 63 was obtained 0.20 g of 2-(1-[(1,3-dimethylbutoxy)carbonyl]ethyl)-2-(3,3,3-trifluoropropyl)malononitrile (hereinafter referred to as the present invention compound (69)).

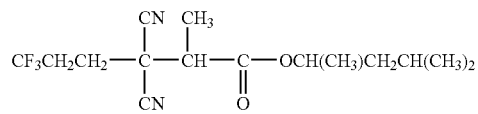

$^1$H-NMR (CDCl$_3$, TMS) δ (ppm): 0.83-0.93 (6H, m), 1.24 (3H, d), 1.23-1.32 (1H, m), 1.48-1.63 (3H, m), 2.16-2.24 (2H, m), 2.47-2.58 (2H, m), 2.91 (1H, q), 5.01-5.16 (1H, m)

PRODUCTION EXAMPLE 70

By using 0.19 g of (2,2-dimethylpropyl) 2-chloropropionate instead of (1-cyano-1-methylethyl) chloroacetate according to Production Example 63 was obtained 0.20 g of 2-(1-[(2,2dimethylpropoxy)carbonyl]ethyl)-2-(3,3,3-trifluoropropyl)malononitrile (hereinafter referred to as the present invention compound (70)).

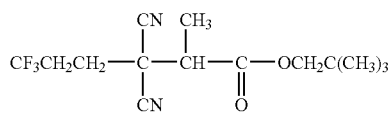

$^1$H-NMR (CDCl$_3$, TMS) δ (ppm): 0.96 (9H, s), 1.62 (3H, d), 2.21-2.30 (2H, m), 2.52-2.59 (2H, m), 3.02 (1H, q), 3.89 (2H, s)

PRODUCTION EXAMPLE 71

By using 0.33 g of methyl 2-bromopropionate instead of ethyl 2-bromopropionate according to Production Example 7 (2) was obtained 0.39 g of 2-[1-(methoxycarbonyl)ethyl]-2-(3,3,3-trifluoropropyl)malononitrile (hereinafter referred to as the present invention compound (71)).

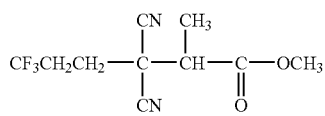

$^1$H-NMR (CDCl$_3$, TMS) δ (ppm): 1.59 (3H, d), 2.18-2.32 (2H, m), 2.55-2.62 (2H, m), 2.98 (1H, q), 3.82 (3H, s)

PRODUCTION EXAMPLE 72

By using 0.54 g of methyl 2-bromobutyrate instead of ethyl 2-bromopropionate according to Production Example 7 (2) was obtained 0.42 g of 2-[1-(methoxycarbonyl)propyl]-2-(3,3,3-trifluoropropyl)malononitrile (hereinafter referred to as the present invention compound (72)).

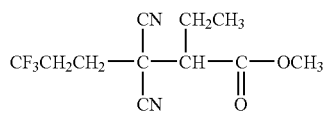

$^1$H-NMR (CDCl$_3$, TMS) δ (ppm): 1.02 (3H, t), 1.97-2.06 (2H, m), 2.14-2.24 (2H, m), 2.49-2.58 (2H, m), 2.77 (1H, q), 3.81 (3H, s)

PRODUCTION EXAMPLE 73

By using 0.17 g of 1,1,1,3,3,3-hexafluoro-2-propanol instead of methanol according to Production Example 12 (2) was obtained 0.02 g of 2-([2,2,2-trifluoro-1-(trifluoromethyl)ethoxy]carbonylmethyl)-2-(3,3,3-trifluoropropyl)malononitrile (hereinafter referred to as the present invention compound (73)).

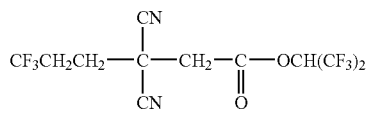

$^1$H-NMR (CDCl$_3$, TMS) δ (ppm): 2.32-2.38 (2H, m), 2.49-2.56 (2H, m), 3.29 (2H, s), 5.82 (1H, q)

PRODUCTION EXAMPLE 74

2.0 g of 2-methylmalononitrile and 4.2 g of ethyl bromoacetate were dissolved in 10 ml of dimethyl sulfoxide. 3.4 g of potassium carbonate was added thereto and stirred for 4 hours at room temperature. Then, to the reaction mixture was added dilute hydrochloric acid, and extracted with ethyl acetate. The organic layer was washed successively with water and saturated brine, dried over anhydrous magnesium sulfate and concentrated under reduced pressure. The residue obtained was subjected to silica gel column chromatography to give 1.0 g of 2-(ethoxycarbonylmethyl)-2-methylmalononitrile (hereinafter referred to as the present invention compound (74)).

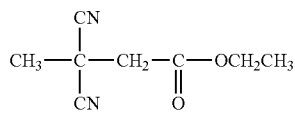

$^1$H-NMR (CDCl$_3$, TMS) δ (ppm): 1.33 (3H, t), 1.92 (3H, s), 2.97 (2H, s), 4.30 (2H, q) Productions of intermediates of the present invention compounds are here exemplified as Reference Production Example.

REFERENCE PRODUCTION EXAMPLE 1

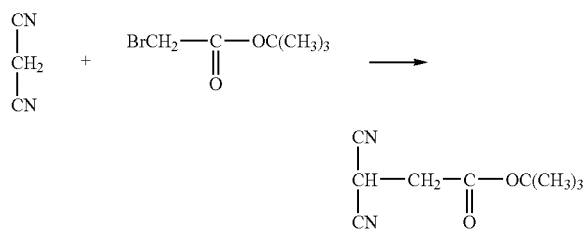

13.2 g of malononitrile was dissolved in 50 ml of N,N-dimethylformamide and 28 g of potassium carbonate was added thereto, followed by stirring for 1 hour at room temperature. To the solution was added 19.6 g of tert-butyl bromoacetate at about 0° C. and stirred for 15 minutes at the same temperature and for additional 4 hours at room temperature. Then, the reaction mixture was poured into water and extracted with ethyl acetate. The organic layer was washed successively with water and saturated brine, dried over anhydrous magnesium sulfate and concentrated under reduced pressure. To the residue obtained was added about 50 ml of mixed solution of hexane and ethyl acetate (hexane/ethyl acetate=3/1) and filtered. The residue obtained by concentrating the filtrate under reduced pressure was subjected to silica gel column chromatography to give 6.13 g of 2-(tert-butoxycarbonylmethyl)malononitrile.

$^1$H-NMR (CDCl$_3$, TMS) δ (ppm): 1.51 (9H, s), 2.98 (2H, d), 4.12 (1H, t)

REFERENCE PRODUCTION EXAMPLE 2

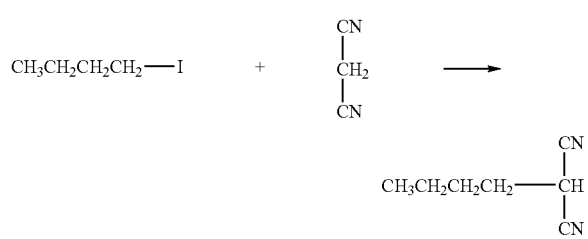

26.4 g of malononitrile was dissolved in 60 ml of N,N-dimethylformamide and 56 g of potassium carbonate was added thereto, followed by stirring for 1 hour at room temperature. To the solution was added 40 g of iodobutane at about 0° C. and stirred for 30 minutes at the same temperature and for additional 4 hours at room temperature. Then, the reaction mixture was poured into water and extracted with ethyl acetate. The organic layer was washed successively with water and saturated brine, dried over anhydrous magnesium sulfate and concentrated under reduced pressure. The residue obtained was subjected to silica gel column chromatography to give 17 g of 2-butylmalononitrile.

$^1$H-NMR (CDCl$_3$, TMS) δ (ppm): 0.97 (3H, t), 1.38-1.48 (2H, m), 1.58-1.69 (2H, m), 2.01-2.06 (2H, m), 3.74 (1H, t)

REFERENCE PRODUCTION EXAMPLE 3

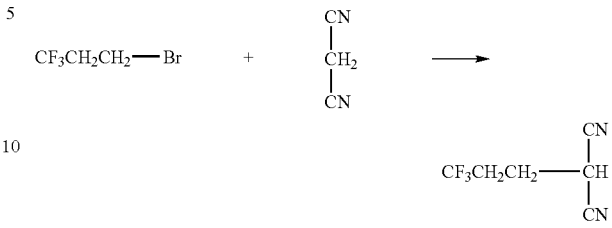

27.6 g of malononitrile was dissolved in 50 ml of N,N-dimethylformamide and 27.6 g of potassium carbonate was added thereto, followed by stirring for 1 hour at room temperature. To the solution was added the mixture of 17.7 g of 1-bromo-3,3,3-trifluoropropane and 20 ml of N,N-dimethylformamide and stirred for 1 hour. Then, the reaction mixture was poured into water and extracted with diethyl ether. The organic layer was washed successively with water and saturated brine, dried over anhydrous magnesium sulfate and concentrated under reduced pressure. The residue obtained was subjected to silica gel column chromatography to give 11.3 g of 2-(3,3,3-trifluoropropyl)malononitrile.

$^1$H-NMR (CDCl$_3$, TMS) δ (ppm): 2.32-2.42 (2H, m), 2.43-2.52 (2H, m), 3.91 (1H, t)

REFERENCE PRODUCTION EXAMPLE 4

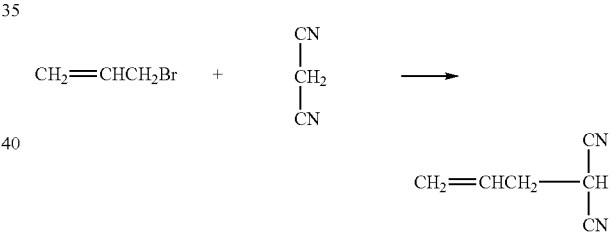

9.3 g of potassium tert-butoxide was added to the mixture of 11 g of malononitrile, 10 g of 3-bromo-1-propene and 1.1 g of tetrabutylammonium bromide under nitrogen atmosphere and stirred for 12 hours at room temperature. Then, the reaction mixture was poured into water and extracted with tert-butyl methyl ether. The organic layer was washed successively with water and saturated brine, dried over anhydrous magnesium sulfate and concentrated under reduced pressure. The residue obtained was subjected to silica gel column chromatography to give 5 g of 2-allylmalononitrile.

$^1$H-NMR (CDCl$_3$, TMS) δ (ppm): 2.75 (2H, dd), 3.79 (1H, t), 5.36-5.45 (2H, m), 5.75-5.94 (1H, m)

REFERENCE PRODUCTION EXAMPLE 5

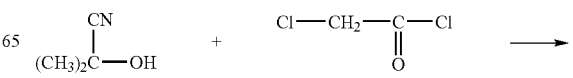

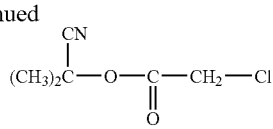

(1) 50 ml of tetrahydrofuran, 10 ml of pyridine and 1.22 g of 4-dimethylaminopyridine were mixed. (Hereinafter, thus obtained solution is referred to as solution F.)

(2) 0.85 g of 2-cyano-2-propanol and solution F were mixed and stirred for 15 minutes at 0° C. To the mixture was added 0.8 ml of chloroacetic chloride and the solution was stirred for 5 minutes at 0° C., additional 2 hours at room temperature and further 1 hour at 70° C. Then, to the reaction mixture was added 1N hydrochloric acid and water, and extracted with ethyl acetate. The organic layer was washed successively with water and aqueous solution of sodium bicarbonate, dried over anhydrous magnesium sulfate and concentrated under reduced pressure. The residue obtained was subjected to silica gel column chromatography to give 0.25 g of (1-cyano-1-methylethyl) chloroacetate.

$^1$H-NMR (CDCl$_3$, TMS) δ (ppm): 1.79 (6H, s), 4.03 (2H, s)

REFERENCE PRODUCTION EXAMPLE 6

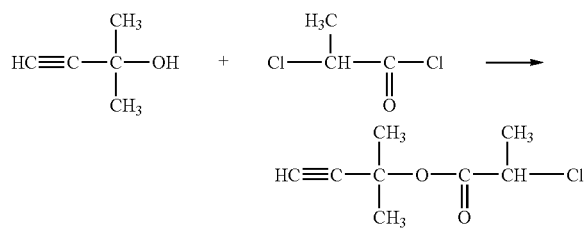

0.84 g of 1,1-dimethyl-2-propynol and solution F were mixed and stirred for 15 minutes at 0° C. To the mixture was added 0.97 ml of 2-chloropropionyl chloride and the solution was stirred for 5 minutes at 0° C., additional 5 hours at room temperature. Then, to the reaction mixture was added 1N hydrochloric acid and water, and extracted with ethyl acetate. The organic layer was washed successively with water and aqueous solution of sodium bicarbonate, dried over anhydrous magnesium sulfate and concentrated under reduced pressure. The residue obtained was subjected to silica gel column chromatography to give 1.06 g of (1,1-dimethyl-2-propynyl) 2-chloropropionate.

$^1$H-NMR (CDCl$_3$, TMS) δ (ppm): 1.68 (3H, d), 1.70 (6H, s), 2.52 (1H, s), 4.31 (1H, q)

REFERENCE PRODUCTION EXAMPLE 7

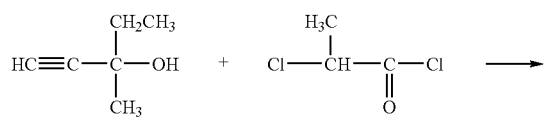

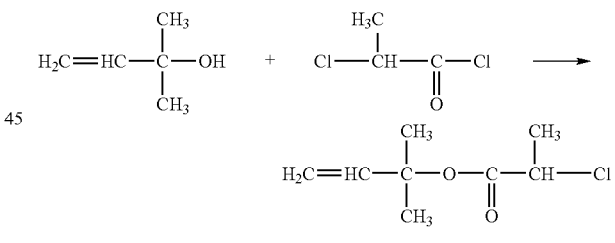

By using 0.98 g of 1-ethyl-1-methyl-2-propynol instead of 1,1-dimethyl-2-propynol according to Reference Production Example 6 was obtained 1.06 g of (1-ethyl-1-methyl-2-propynyl) 2-chloropropionate.

$^1$H-NMR (CDCl$_3$, TMS) δ (ppm): 1.02 (3H, t), 1.64-1.72 (5H, m), 1.83-2.02 (2H, m), 2.52 (1H, s), 4.32 (1H, q)

REFERENCE PRODUCTION EXAMPLE 8

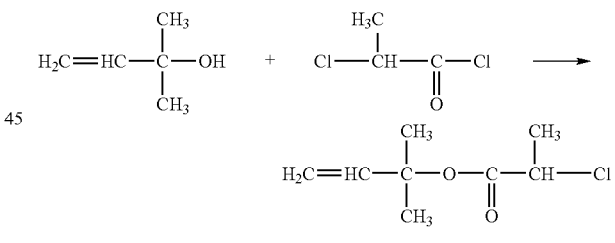

By using 0.85 g of 2-cyano-2-propanol instead of 1,1-dimethyl-2-propynol according to Reference Production Example 6 was obtained 1.15 g of (1-cyano-1-methylethyl) 2-chloropropionate.

$^1$H-NMR (CDCl$_3$, TMS) δ (ppm): 1.70 (3H, d), 1.79 (6H, s), 4.32 (1H, q)

REFERENCE PRODUCTION EXAMPLE 9

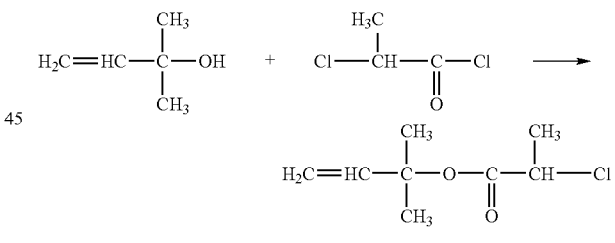

By using 0.86 g of 1,1-dimethyl-2-propenol instead of 1,1-dimethyl-2-propynol according to Reference Production Example 6 was obtained 0.69 g of (1,1-dimethyl-2-propenyl) 2-chloropropionate.

$^1$H-NMR (CDCl$_3$, TMS) δ (ppm): 1.62 (3H, d), 4.25 (1H, q), 5.14 (2H, dd), 6.03 (1H, dd)

REFERENCE PRODUCTION EXAMPLE 10

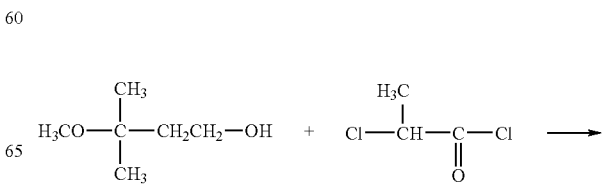

-continued

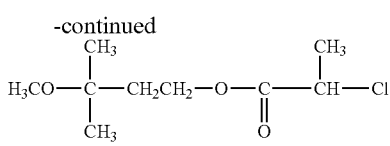

By using 1.19 g of 3-methyl-3-methoxybutanol instead of 1,1-dimethyl-2-propynol according to Reference Production Example 6 was obtained 1.22 g of (3-methyl-3-methoxybutyl) 2-chloropropionate.

$^1$H-NMR (CDCl$_3$, TMS) δ (ppm): 1.12 (6H, s), 1.62 (3H, d), 1.83 (2H, t), 3.13 (3H, s), 4.23 (2H, t), 4.32 (1H, q)

REFERENCE PRODUCTION EXAMPLE 11

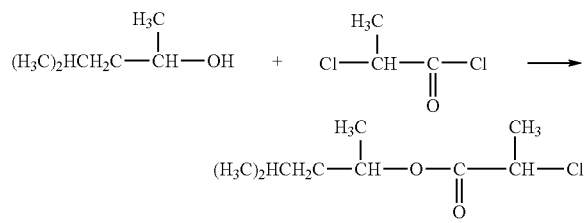

By using 1.02 g of 1,3-dimethylbutanol instead of 1,1-dimethyl-2-propynol according to Reference Production Example 6 was obtained 1.10 g of (1,3-dimethylbutyl) 2-chloropropionate.

$^1$H-NMR (CDCl$_3$, TMS) δ (ppm): 0.89-0.92 (6H, m), 1.26 (3H, d), 1.28-1.32 (1H, m), 1.50-1.69 (3H, m), 4.31 (1H, q), 4.97-5.05 (1H, m)

REFERENCE PRODUCTION EXAMPLE 12

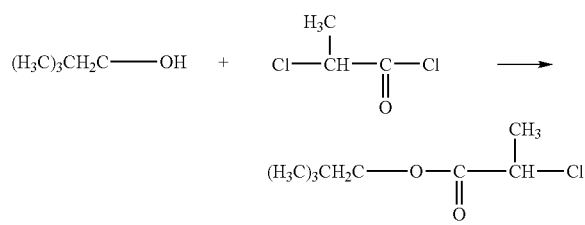

By using 0.88 g of 2,2-dimethylpropanol instead of 1,1-dimethyl-2-propynol according to Reference Production Example 6 was obtained 0.96 g of (2,2-dimethylpropyl) 2-chloropropionate.

$^1$H-NMR (CDCl$_3$, TMS) δ (ppm): 0.94 (9H, s), 1.69 (3H, d), 3.83 (2H, q), 4.38 (1H, q)

REFERENCE PRODUCTION EXAMPLE 13

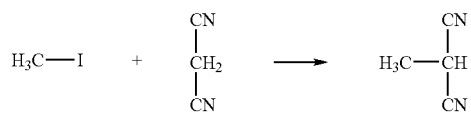

9.3 g of iodomethane and 4.3 g of malononitrile were dissolved in 30 ml of dimethyl sulfoxide. 9.0 g of potassium carbonate was added thereto and stirred for 5 hours at room temperature. Then, to the reaction mixture was added dilute hydrochloric acid and extracted with ethyl acetate. The organic layer was washed successively with water and saturated brine, dried over anhydrous magnesium sulfate and concentrated under reduced pressure. The residue obtained was subjected to silica gel column chromatography to give 2.0 g of 2-methylmalononitrile.

$^1$H-NMR (CDCl$_3$, TMS) δ (ppm): 1.78 (3H, d), 3.78 (1H, q)

Formulation Examples are exemplified below. In addition, "part" means a part by weight. The present invention compounds are designated by their compound numbers shown above.

FORMULATION EXAMPLE 1

9 Parts of each of the present invention compounds (1) to (74) are dissolved in 37.5 parts of xylene and 37.5 parts of dimethylformamide, and 10 parts of polyoxyethylene styryl phenyl ether and 6 parts of calcium dodecylbenzenesulfonate are added thereto, followed by well stirring and mixing, to give an emulsion for each compound.

FORMULATION EXAMPLE 2

To 40 parts of each of the present invention compounds (1) to (74) are added 5 parts of SORPOL 5060 (registered trade name for TOHO KAGAKU KOGYO), followed by well mixing. To the mixture are added 32 parts of CARPLEX #80 (registered trade name for SHIONOGI & Co., synthetic hydrated silicone oxide fine powder) and 23 parts of 300 mesh diatomaceous earth, followed by mixing with juice mixer, to give a wettable powder for each compound.

FORMULATION EXAMPLE 3

To 3 parts of each of the present invention compounds (1) to (74) are added 5 parts of synthetic hydrated silicon oxide fine powder, 5 parts of sodium dodecylbenzenesulfonate, 30 parts of bentonite and 57 parts of clay, followed by well stirring and mixing. Then an appropriate amount of water is added to this mixture, followed by further stirring, granulating with a granulator and air drying, to give a granule for each compound.

FORMULATION EXAMPLE 4

4.5 Parts of each of the present invention compounds (1) to (74), 1 part of synthetic hydrated silicon oxide fine powder, 1 part of Doriresu B (Sankyo Co., Ltd.) as a flocculant and 7 parts of clay are well mixed with a mortar, followed by stirring and mixing with a juice mixer. To the resulting mixture is added 86.5 parts of cut clay, followed by well stirring and mixing, to give a powder for each compound.

FORMULATION EXAMPLE 5

10 Parts of each of the present invention compounds (1) to (74), 35 parts of white carbon containing 50 parts of polyoxyethylene alkyl ether sulfate ammonium salt and 55 parts of water are mixed and pulverized by the wet grinding method to give a formulation for each compound.

FORMULATION EXAMPLE 6

0.5 Parts of each of the present invention compounds (1) to (74) are dissolved in 10 parts of dichloromethane, and the resulting solution is mixed with 89.5 parts of Iso-Par M (iso-paraffine: registered trade name for EXXON CHEMICAL LTD) to give an oil solution.

FORMULATION EXAMPLE 7

0.1 Parts of each of the present invention compounds (1) to (74) and 49.9 parts of NEO-CHIOZOL (CHUO KASEI Co., LTD) are charged into aerosol can, and aerosol valve is fixed to the can. Then 25 parts of dimethyl ether and 25 parts of LPG are filled in the can, followed by shaking and fitting an actuator on it, to give an oil aerosol.

FORMULATION EXAMPLE 8

0.6 Parts of each of the present invention compounds (1) to (74), 0.01 parts of BHT, 5 parts of xylene, 3.39 parts of deodorized kerosene and 1 part of emulsifier [Atmos 300 (registered trade name for ATMOS CHEMICAL LTD)] are mixed and dissolved. The resulting solution and 50 parts of distilled water are charged into aerosol container, and a valve is fixed to the container. 40 Parts of propellant (LPG) are charged under pressure through the valve to give an aqueous aerosol.

The following test example will demonstrate that the present invention compounds have an excellent pesticidal activity as active ingredient of a composition for controlling pests. The present invention compounds are designated by their compound numbers shown above.

In addition, in order to clarify the controlling activity for pests of the present invention compounds, 2-[2-(ethoxycarbonyl)ethyl]malononitrile (hereinafter referred to as the reference compound (1)), which is disclosed in J. Org. Chem., 36, 16 (1971) pp 2385-2387, was used as control compound.

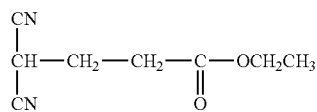

TEST EXAMPLE 1

The formulation obtained according to Formulation Example 5 using the present invention compound (74) and the reference compound (1) respectively, was diluted with water so that the active ingredient concentration came to 2000 ppm to prepare a pesticidal solution for test.

At the same time, 50 grams of molding Bonsoru 2 (available from Sumitomo Chemical Co., Ltd.) was put into a polyethylene cup, and 10 to 15 seeds of rice were planted in the polyethylene cup. The rice plants were grown until the second foliage leaves developed and then cut into the same height of 5 cm. The pesticidal solution for test prepared above was sprayed at the rate of 20 ml/cup to these rice plants. After the pesticidal solution sprayed onto the rice plants were dried, they were put into a plastic cup for escape prevention of test pests, and thirty first-instar larvae of *Nilaparvata lugens* were set free on the rice plants, followed by covering the plastic cup with a lid. Then the plastic cup was left in a greenhouse (25° C.). On the sixth day after the release of larvae of *Nilaparvata lugens*, the number of parasitic *Nilaparvata lugens* on the rice plants was examined.

As a result, in the treatment with the present invention compounds (74), the number of parasitic *Nilaparvata lugens* was 3 or fewer. On the contrary, in the treatment with the reference compound (1), the number of parasitic *Nilaparvata lugens* was 20 or more.

TEST EXAMPLE 2

The formulation obtained according to Formulation Example 5 using the present invention compounds (24), (25), (28), (29), (31), (34), (35), (37), (40), (44)-(46), (51), (53), (55), (57)-(62), (64), (65), (66), (69) and (70) respectively, was diluted with water so that the active ingredient concentration came to 500 ppm to prepare a pesticidal solution for test.

At the same time, 50 grams of molding Bonsoru 2 (available from Sumitomo Chemical Co., Ltd.) was put into a polyethylene cup, and 10 to 15 seeds of rice were planted in the polyethylene cup. The rice plants were grown until the second foliage leaves developed and then cut into the same height of 5 cm. The pesticidal solution for test prepared above was sprayed at the rate of 20 ml/cup to these rice plants. After the pesticidal solution sprayed onto the rice plants were dried, they were put into a plastic cup for escape prevention of test pests, and thirty first-instar larvae of *Nilaparvata lugens* were set free on the rice plants, followed by covering the plastic cup with a lid. Then the plastic cup was left in a greenhouse (25° C.). On the sixth day after the release of larvae of *Nilaparvata lugens*, the number of parasitic *Nilaparvata lugens* on the rice plants was examined.

As a result, in the treatment with each of the present invention compounds (24), (25), (28), (29), (31), (34), (35), (37), (40), (44)-(46), (51), (53), (55), (57)-(62), (64), (65), (66), (69) and (70), the number of parasitic *Nilaparvata lugens* was not greater than 3.

TEST EXAMPLE 3

The formulation obtained according to Formulation Example 5 using the present invention compounds (23) was diluted with water so that the active ingredient concentration came to 500 ppm to prepare a pesticidal solution for test.

At the same time, molding Aisai 1 (available from KATAOKA TIKKARIN Co., Ltd.) was put into a 90 ml polyethylene cup, and seeded with cucumber. The plant was grown until the first true leaf was developed, on which about twenty *Aphis gossypii* were allowed to be parasitic. On the next day, the above pesticidal solution for test was sprayed at a ratio of 20 ml/cup on the cucumber plant. On the sixth day after the application, the number of *Aphis gossypii* was examined.

As a result, in the treatment with the present invention compound (23), the number of parasitic *Aphis gossypii* on the sixth day after the treatment was not greater than 3.

TEST EXAMPLE 4

The formulation obtained according to Formulation Example 5 using the present invention compounds (1), (7), (13)-(17), (20), (28), (32), (36), (37), (39), (44)-(46), (53), (55), (57)-(62), (64)-(70) and (71) respectively, was diluted with water so that the active ingredient concentration came to 500 ppm to prepare a pesticidal solution for test.

On the bottom of a polyethylene cup having a diameter of 5.5 cm, a filter paper having the same diameter was laid, and 0.7 ml of the above pesticidal solution for test was added dropwise on the filter paper, followed by putting 30 mg of sucrose on it uniformly as a bait. Ten female *Musca domestics* imagoes were set free in the polyethylene cup and covered it with a lid. After 24 hours, the number of surviving *Musca domestics* was examined and the rate of dead pests was calculated.

As a result, in the treatment with each of the present invention compounds (1), (7), (13)-(17), (20), (28), (32), (36), (37), (39), (44)-(46), (53), (55), (57)-(62), (64)-(70) and (71), the rate of dead pests was 90% or more.

TEST EXAMPLE 5

The formulation obtained according to Formulation Example 5 using the present invention compounds (1), (25), (28), (36), (39), (40), (44)-(46), (47), (57), (58), (64), (65) and (67) respectively, was diluted with water so that the active ingredient concentration came to 500 ppm to prepare a pesticidal solution for test.

On the bottom of a polyethylene cup having a diameter of 5.5 cm, a filter paper having the same diameter was laid, and 0.7 ml of the above pesticidal solution for test was added dropwise on the filter paper, followed by putting 30 mg of sucrose on it uniformly as a bait. Two male *Blattalla germanica* imagoes were set free in the polyethylene cup and covered it with a lid. After 6 days, the number of surviving *Blattella germanica* was examined and the rate of dead pests was calculated.

As a result, in the treatment with each of the present invention compounds (1), (25), (28), (36), (39), (40), (44)-(46), (47), (57), (58), (64), (65) and (67), the rate of dead pests was 100%.

TEST EXAMPLE 6

The formulation obtained according to Formulation Example 5 using the present invention compounds (7), (8)-(11), (14)-(16), (20), (21), (24)-(26), (28), (29), (31), (37)-(39), (44)-(47), (51), (53), (55), (57), (58), (60)-(67), (69), (70) and (71) respectively, was diluted with water so that the active ingredient concentration came to 500 ppm to prepare a pesticidal solution for test.

0.7 ml of above pesticidal solution for test was added to 100 ml of ion exchanged water (active ingredient concentration: 3.5 ppm). Twenty last-instar larvae of *Culex pipiens pallens* were set free in the solution. After one day, the number of surviving *Culex pipiens pallens* was examined and the rate of dead pests was calculated.

As a result, in the treatment with each of the present invention compounds (7), (8)-(11), (14)-(16), (20), (21), (24)-(26), (28), (29), (31), (37)-(39), (44)-(47), (51), (53), (55), (57), (58), (60)-(67), (69), (70) and (71), the rate of dead pests was 100%.

INDUSTRIAL APPLICABILITY

Pests such as insect pests, acarine pests, nematode pests and the like can be controlled effectively by the present invention.

The invention claimed is:

1. A malononitrile compound represented by the formula (A):

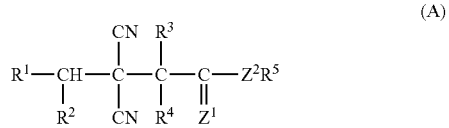

wherein, $R^1$ represents hydrogen atom, C1 to C3 haloalkyl, C2 to C6 alkenyl that may be substituted with halogen, C2 to C6 alkynyl that may be substituted with halogen, C3 to C6 cycloalkyl that may be substituted with halogen or C2 to C4 cyanoalkyl; $R^2$ represents hydrogen atom or C1 to C6 alkyl that may be substituted with halogen; $R^3$ represents hydrogen atom or C1 to C6 alkyl; $R^4$ represents hydrogen atom or C1 to C6 alkyl; $R^5$ represents C1 to C8 alkyl that may be substituted with halogen, C3 to C8 alkenyl that may be substituted with halogen, C3 to C8 alkynyl that may be substituted with halogen, C3 to C6 cycloalkyl that may be substituted with halogen, C1 to C3 alkyl which is substituted with optionally halogenated C3 to C6 cycloalkyl, C2 to C8 cyanoalkyl or C3 to C8 alkoxyalkyl, or $R^4$ and $R^5$ may be combined at their terminal and represent ethylene that may be substituted with C1 to C3 alkyl or trimethylene that may be substituted with C1 to C3 alkyl; and $Z^1$ and $Z^2$, which are the same or different, each independently represent oxygen atom or sulfur atom.

2. The malononitrile compound according to claim 1 wherein, in the formula (A), $R^4$ is hydrogen atom or C1 to C6 alkyl, $R^5$ is C1 to C6 alkyl that may be substituted with halogen, C3 to C6 alkenyl that may be substituted with halogen, C3 to C6 alkynyl that may be substituted with halogen, C3 to C6 cycloalkyl that may be substituted with halogen or C1 to C3 alkyl which is substituted with optionally halogenated C3 to C6 cycloalkyl, or $R^4$ and $R^5$ may be combined at their terminal and represent ethylene that may be substituted with C1 to C3 alkyl or trimethylene that may be substituted with C1 to C3 alkyl.

3. The malononitrile compound according to claim 1 wherein, in the formula (A), $R^1$ is 2,2,2-trifluoroethyl, vinyl, 2-methyl-1-propenyl, 2,3,3-trifluoro-2-propenyl, cyclopropyl or 2,2-dichloro-1-cyclopropyl.

4. A pesticide composition comprising the malononitrile compound according to claim 1 as active ingredient and an inert carrier.

5. A method for controlling pests comprising applying an effective dose of the malononitrile compound according to claim 1 to pests or habitat of pests.

6. The malononitrile compound according to claim 2 wherein, in the formula (A), $R^1$ is C1 to C3 haloalkyl, C2 to C6 alkenyl that may be substituted with halogen, C2 to C6 alkynyl that may be substituted with halogen, C3 to C6 cycloalkyl that may be substituted with halogen or C2 to C4 cyanoalkyl.

* * * * *